(12) United States Patent
Vertesy et al.

(10) Patent No.: US 7,067,112 B2
(45) Date of Patent: Jun. 27, 2006

(54) **CEPHAIBOLS: NOVEL ANTIPARASITICS FROM *ACREMONIUM TUBAKII*, PROCESS FOR THEIR PRODUCTION, AND USE THEREOF**

(75) Inventors: Laszlo Vertesy, Eppstein (DE); Michael Kurz, Hofheim (DE); Matthias Schiell, Brechen (DE); Joachim Hofmann, Bad Camberg (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 402 days.

(21) Appl. No.: 10/411,144

(22) Filed: Apr. 11, 2003

(65) Prior Publication Data

US 2003/0203848 A1 Oct. 30, 2003

Related U.S. Application Data

(62) Division of application No. 09/563,505, filed on May 3, 2000, now Pat. No. 6,582,949.

(30) Foreign Application Priority Data

May 5, 1999 (DE) ................................ 199 20 816

(51) Int. Cl.
*A61K 49/00* (2006.01)
*A61K 38/10* (2006.01)
*C07K 7/08* (2006.01)

(52) U.S. Cl. ........................... 424/9.1; 514/13; 514/14; 530/326; 530/412; 435/243

(58) Field of Classification Search ................ 424/9.1; 514/13, 14; 435/243; 530/326, 412
See application file for complete search history.

(56) References Cited

U.S. PATENT DOCUMENTS 3,657,419 A 4/1972 Thirumalachar

OTHER PUBLICATIONS

Kenneth L. Rinehart, Jr. et al., "Fast atom bombardment mass spectrometry; a promising tool for structural studies," *Trends in Analytical Chemistry*, vol. 2, No. 1, pp. 10-14, (1983).
Ramesh C. Pandey, et al. "Structure of the Peptide Antibiotic Antiamoebin II," *The Journal of Antibiotics*, Communications to the editor, vol. XXXI, No. 3, pp. 241-243 (1978).
Gary J. Sharman, et al., "Structural elucidation of XR586, a peptaibol-like antibiotic from *Acremonium persicinum*," *Biochem. Journal*, vol. 320, pp. 723-728 (1996).

Andreas Jaworski, et al., "New Sequences and New Fungal Procedures of Peptaibol Antibiotics Antiamoebins," *J. Peptide Sci.*, vol. 6, pp. 149-167 (2000).
Hans Brückner, et al., "The Sequences of the Membrane-Modifying Peptide Antibiotic Trichotoxin A-40," *Angew. Chem. Int. Ed. Engl.*, vol. 18, No. 6, pp. 476-477 (1979).
Shigenori Kumazawa, et al., "Structural Elucidation of Aibellin, a New Peptide Antibiotic with Efficiency Enhancing Activity on Rumen Fermentation," *The Journal of Antibiotics*, vol. 47, No. 10, pp. 1136-1144 (1994).
Michael Ritzau, et al., "Ampullosporin, a New Peptaibol-type Antibiotic from *Sepedonium ampullosporum* HKI-0053 with Neuroleptic Activity in Mice," *The Journal of Antibiotics*, vol. 50, No. 9, pp. 722-728 (1997).
C.F. Snook, et al., "The structure and function of antiamoebin I, a proline-rich membrane-active polypeptide," *Structure*, vol. 6, No. 6, pp. 783-792 (1998).
Toshihiro Chikanishi et al., "Clonostachin, a Novel Peptaibol That Inhibits Platelet Aggregation," *The Journal of Antibiotics*, vol. 50, No. 2, pp. 105-110 (1997).
A.D. Argoudelis, et al., "Emerimicins II, III and IV, Antibiotics Produced by *Emericellopsis microspora* in Media Supplemented with Trans-4-n-Propyl-L-Proline," *The Journal of Antibiotics*, vol. XXVII, No. 4, pp. 274-282 (1974).
A.D. Argoudelis, et al., "Zervamicins* I and II, Polypeptide Antibiotics Produced by *Emericellopsis salmosynnemata*," *The Journal of Antibiotics*, vol. XXVII, No. 5, pp. 321-328 (1974).

*Primary Examiner*—Kathleen M. Kerr
*Assistant Examiner*—Chih-Min Kam
(74) *Attorney, Agent, or Firm*—Finnegan, Henderson, Farabow, Garrett and Dunner, L.L.P.

(57) ABSTRACT

The invention relates to compounds of the formula I

AcPhe-Aib-Aib-Aib-x-w-Leu-y-Aib-Hyp-Gln-z-Hyp-Aib-Pro-R (I)

in which R is Phe-ol or Phe-al and w, x, y, and z have the following meanings:
a) w is Gly or Ala; x is Aib and y and z are Iva;
b) w is Gly; x, y and z are Iva;
c) w is Gly; x and z are Aib and y is Iva;
d) w is Gly; x, y and z are Aib; or
e) w is Gly; x and y are Aib and z is Iva;
or of the formula II AcPhe-Iva-Gln-Aib-Ile-Thr-Aib-Leu-Aib-x-Gln-Aib-Hyp-Aib-Pro-Phe-Ser, (II)

wherein x is Hyp or Pro, which are synthesized by *Acremonium tubakii* FH 1685 DSM 12774 during fermentation and released into the culture medium, a process for the isolation of the cephaibols from the culture medium, and their purification, and the use of the cephaibols as pharmacologically active compounds, in particular for the control of parasites.

12 Claims, No Drawings

CEPHAIBOLS: NOVEL ANTIPARASITICS FROM ACREMONIUM TUBAKII, PROCESS FOR THEIR PRODUCTION, AND USE THEREOF

This application is a divisional of U.S. application Ser. No. 09/563,505, filed May 3, 2000, now U.S. Pat. No. 6,582,949, which claims the benefit of German Application No. 19920816.6 filed May 5, 1999, both of which are incorporated by reference in their entirety.

FIELD OF THE INVENTION

The invention relates to novel peptaibol antibiotics, called cephaibols, which are synthesized from *Acremonium tubakii* FH 1685 DSM 12774 during fermentation and released into the culture medium, a process for the isolation of the cephaibols from the culture medium and their purification, and the use of the cephaibols as pharmacologically active compounds, in particular for the control of parasites.

BACKGROUND OF THE INVENTION

Parasitoses are widespread and cause a wide spectrum of pathological effects in humans and animals, which range from slight physiological disturbances to severe, even fatal disorders. Nowadays, many intensively researched parasite disorders are known which threaten the health and the life of humans, their pets, and farm animals.

Globally, the weakening of the immune system is to be increasingly found in millions of humans. This group of people is so massively affected by opportunistic parasites that, annually, millions of deaths are mourned. In the age of long-distance travel, even in non-third world countries, which normally have a high standard of hygiene, exotic parasites have to be expected. This has its origins in the fact that there is an ever increasing trend to go on trekking trips under local hygiene conditions and that—because of the supposed safety in one's own country—there is a loss of the feeling/knowledge about hygiene dangers in other countries. In addition to the protection of human health, protection of animals from the suffering and pain caused by parasitoses is required either by a cure or, if possible, by prevention. Economic reasons especially come to bear in farm animal husbandry, where, owing to unfavorable conditions for the keeping and feeding of animals (e.g., in certain forms of mass animal husbandry), parasitic disorders occur which contribute to a quantitative loss (reduction in yield of meat, number of eggs, racing pace) or a qualitative loss (quality of meat and wool). The great damage that is caused by parasitoses in humans and animals makes their control desirable, if not indispensable, in the interests of health and economy.

Parasites are unicellular or multicellular organisms which reside temporarily or permanently in (endoparasites) or on (ectoparasites) foreign organisms and live at the expense of the host. In humans and animals, many parasites lead to subacute and also to dramatic disorders. The unicellular parasites include the protozoa, such as, for example, plasmodia (malaria pathogen), trypanosomes (Chagas disease pathogen), amoebae, trichomonads or toxoplasmae. Important unicellular parasites are the endo-parasitic worms (helminths), of which the threadworms (nematodes), tapeworms (cestodes) and leeches (trematodes) can cause serious damage in humans and animals. The multicellular ectoparasites include ticks, mites, lice, fleas and other organisms. Although there are a large number of agents available for the control and treatment of parasitic disorders (antiparasitics), on the one hand because of the side effects of these agents and on the other hand because of the increasing formation of resistance, there is a great need for novel, highly effective protozoicides, anthelminthics, and other parasiticides. Infestation with parasites in particular affects the population of the tropical regions; the number of those affected here is estimated at many hundreds of millions of people, in addition to the considerable damage in the agricultural field.

The use of chemical substances, whose activity against individual parasites or relatively large groups of parasites is known and which are toxicologically acceptable in the host (humans, animals) still have overriding importance in parasite control.

According to their spectrum of action, a differentiation is made between anthelminthics acting against helminths, antiprotozoals active against protozoa, insecticides active against insects, and acaricides active against mites (acaria); the last two groups are also summarized under the term ectoparasiticides.

There has been an increase in pharmaceutical resistance caused by long term and intensive use, particularly in modern mass animal husbandry. There has also been an increased occurrence of severe side effects to present medications, in particular of continuous medication of people who, within the framework of progressive globalization, have to work for a relatively long time in the tropics and subtropics. These factors combined with the high cost of prophylaxis/therapy with certain chemotherapeutics makes the search for inexpensive classes of substances having a different mechanism of action and better tolerability essential. Antiparasitics are also needed which are not only effective, but also economically preparable in large amounts, and moreover, environmentally friendly.

Bacteria and fungi via their secondary metabolism by means of nonribosomal peptide synthetases produce peptides having up to 20 amino acids, and in some cases structurally unusual amino acids. Many of the previously known secondary metabolites having a peptide structure possess interesting biological actions as antibiotics, enzyme inhibitors, cardiotonics, immunomodulators, insecticides, nematocides and many others (see, for example, Gräfe, U. *Biochemie der Antibiotika*, Spektrum Heidelberg, 1992).

Within the structural class of peptide active compounds, the so-called peptaibols are distinguished in that they unusually contain many amino acids (up to 20, among them a high proportion of α-aminobutyric acid (Brückner, H., König, W. A., Greiner, M., Jung, G. Angew. *Chem. Int Ed. Engl.* 18:476–477(1979)). In addition, peptaibols are very often acetylated at the N terminus and contain a radical having an alcohol group (e.g., phenylalaminol) or an aldehyde group at the C terminus.

Examples of peptaibols, as addressed above, are aibellin [*J. Antibiotics* 47:1136–1144 (1994)]; ampullosporin [*J. Antibiotics* 50:72–728, (1997)]; antiamoebin [*Structure* 6:783–792 (1998)]; clonostachin [J. Antibiotics 50:105–110 (1997)]; emerimicins [*J. Antibiotics,* 27:274–282 (1974)] or zervamicins [*J. Antibiotics,* 27:321–328 (1974)]. These peptaibols are synthesized by very different strains of the genera *Emericellopsis, Trichoderma, Apiocrea,* and many others. They display their antibiotic activity against gram-positive bacteria, against some types of fungi, and against amoebae. The antipyretic and neuroleptic action of ampullosporin has moreover been described.

The previously known peptide active compounds, however, often have disadvantages that are manifested in unsatisfactory potency of action, high toxicity, and/or undesired side effects.

SUMMARY OF THE INVENTION

The object of the invention is therefore to search for novel microbial peptide active compounds having improved properties and/or novel mechanisms of action.

This object is achieved, according to the invention, by fermenting the strain *Acremonium tubakii* FH 1685 DSM 12774 in a nutrient solution having a carbon and nitrogen source, as well as the customary inorganic salts, until the novel peptaibols, called cephaibols, accumulate in the culture medium, then isolating the cephaibols from the culture medium, and optionally, separating the cephaibols into the individual active peptide compounds. The isolated cephaibols are pharmacologically active and are, thus, suitable for use as pharmaceuticals. Because of their antiparasitic properties, in particular their strong anthelmintic activity and insecticidal action on ectoparasites, they can be employed, in particular, as antibiotics having action against endo- and ectoparasites in animals and in humans.

The invention thus relates to

1. A compound of the formula I (SEQ ID NO:9)

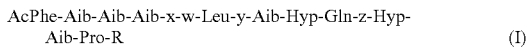

wherein R is Phe-ol or Phe-al and w, x, y, and z have the following meanings:
a) w is Gly or Ala; x is Aib and y and z are Iva;
b) w is Gly; x, y and z are Iva;
c) w is Gly; x and z are Aib and y is Iva;
d) w is Gly; x, y and z are Aib; or
e) w is Gly; x and y are Aib and z is Iva;

and their physiologically tolerable salts; or a compound of the formula II (SEQ ID NO:10)

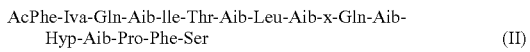

wherein x is Hyp or Pro; and their physiologically tolerable salts.

2. A process for the preparation of one or more compounds of the formula I or II, which comprises fermenting *Acremonium tubakii*, in particular *Acremonium tubakii* FH 1685 DSM 12774, in a culture medium until one or more compounds of the formula I or II accumulate in the culture medium and isolating these from the culture medium.

3. The use of a compound of the formula I or II as a pharmacologically active substance, in particular as an antibiotic against human or animal parasites, preferably against helminths.

4. A pharmaceutical preparation for use in humans and/or in animals, comprising one or more compounds of the formula I or II.

DETAILED DESCRIPTION OF THE INVENTION

In the following, the invention is described in detail, in particular in its preferred embodiments.

Compounds of the formula I or II are also designated as peptide active compounds or cephaibols.

In the following sequences, AcPhe is N-acetylphenylalanine, Aib is α-aminoisobutyric acid, Ala is alanine, Iva is isovaline, Hyp is hydroxyproline, Phe-ol is phenylalaninol, Phe-al is phenylalaninal, Phe is phenylalanine, Gly is glycine, Leu is leucine, Gln is glutamine, Pro is proline, Ile is isoleucine, Thr is threonine and Ser is serine.

Cephaibol A designates a compound of the formula I, in which

R is Phe-ol, w is Gly, x is Aib and y and z are Iva.

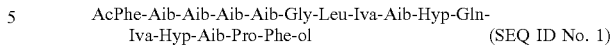

Cephaibol A1 designates a compound of the formula I, in which

R is Phe-ol, w is Ala, x is Aib and y and z are Iva.

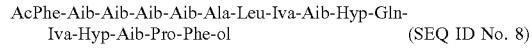

Cephaibol B designates a compound of the formula I, in which

R is Phe-ol, w is Ala and x, y and z are Iva.

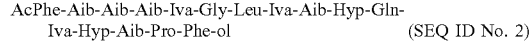

Cephaibol C designates a compound of the formula I, in which

R is Phe-ol, w is Ala, x and z are Aib and y is Iva.

Cephaibol D designates a compound of the formula I, in which

R is Phe-ol, w is Ala and x, y and z are Aib.

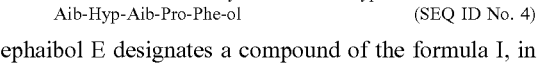

Cephaibol E designates a compound of the formula I, in which

R is Phe-ol, w is Ala, x and y are Aib and z is Iva.

Cephaibol P designates a compound of the formula II, in which x is Hyp.

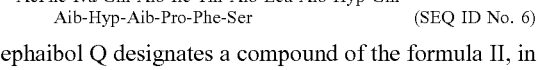

Cephaibol Q designates a compound of the formula II, in which x is Pro.

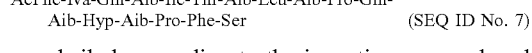

The cephaibols according to the invention are produced by *Acremonium tubakii*, preferably by *Acremonium tubakii* FH 1685 DSM 12774. *Acremonium tubakii* FH 1685 DSM 12774 possesses a beige-red mycelium and is characterized by the conidiophores characteristic of *Acremonium* species.

An isolate was deposited at the Deutsche Sammlung von Mikroorganismen und Zellkulturen GmbH, Mascheroder Weg 1B, D 38124 Brunswick, Germany, according to the rules of the Budapest Convention, on Mar. 31, 1999, under the following number: *Acremonium tubakii* FH 1685 DSM 12774.

In a nutrient solution (also called a culture medium) which contains a carbon source and a nitrogen source and the customary inorganic salts, *Acremonium tubakii* FH 1685 DSM 12774 produces one or more of the compounds of the formula I or II according to the invention.

Instead of the strain *Acremonium tubakii* FH 1685 DSM 12774, its mutants and variants can also be employed which synthesize one or more compounds of the cephaibols according to the invention. Such mutants can be produced in a known manner by physical means, for example, irradiation, such as with ultraviolet or X-rays, or chemical mutagens, such as, for example, ethyl methanesulfonate (EMS), 2-hydroxy-4-methoxybenzophenone (MOB), or N-methyl-N'-nitro-N-nitrosoguanidine (MNNG) or using genetic engineering methods.

Screening for mutants and variants that synthesize one or more of the cephaibols according to the invention is carried out according to the following scheme:

separation of the mycelium after fermentation;

extraction of the mycelium with an organic solvent;

extraction of the cephaibols from the culture filtrate using solid phases or water-immiscible organic solvents;

analysis by means of HPLC, TLC or by testing the biological activity.

The fermentation conditions described below apply to *Acremonium tubakii*, the deposited isolate *Acremonium tubakii* FH 1685 DSM 12774, and mutants and variants of these.

The process according to the invention can be employed for fermentation on a laboratory scale (milliliter to liter range) and on an industrial scale (cubic meter scale). If not stated otherwise, all percentages relate to weight. Mixing ratios, in the case of liquids, relate to volume, if no other details are given.

In a culture medium which contains a carbon source and a nitrogen source and the customary inorganic salts, *Acremonium tubakii* FH 1685 DSM 12774 produces compounds of formula I or II according to the invention.

Preferred carbon sources suitable for aerobic fermentation are assimilable carbohydrates and sugar alcohols, such as glucose, lactose, sucrose or D-mannitol and carbohydrate-containing natural products, such as, for example, malt extract. Possible nitrogen-containing nutrients are: amino acids, peptides and proteins and their degradation products, such as peptones or tryptones, in addition meat extracts, yeast extracts, ground seeds, for example, of corn, wheat, beans, soybeans or the cotton plant, distillation residues from alcohol production, meat meals or yeast extracts, but also ammonium salts and nitrates. Inorganic salts which the nutrient solution can contain are, for example, chlorides, carbonates, sulfates or phosphates of the alkali or alkaline earth metals, iron, zinc, cobalt and manganese.

The formation of the cephaibols according to the invention proceeds particularly well in a culture medium that contains approximately 0.1 to 5%, preferably 0.3 to 2%, of yeast extract and 0.2 to 5%, preferably 0.5 to 3%, of sucrose and 0.1 to 10 g/l, preferably 0.2 to 1.0 g/l, of magnesium sulfate and 0.05 to 1.0 g/l, preferably 0.1 to 0.5 g/l, of potassium or sodium dihydrogenphosphate and 0.05 to 1.0 g/l, preferably 0.1 to 1.0 g/l, of sodium nitrate and 0.01 to 0.1 g/l, preferably 0.02 to 0.1 g/l, of potassium chloride and 0.01 to 100 µm, preferably 5 to 20 µm, of iron sulfate and traces of zinc sulfate and copper sulfate. The details in % are in each case based on the weight of the entire culture medium.

In the culture medium, *Acremonium tubakii* FH 1685 DSM 12774 forms a mixture of cephaibols. Depending on the composition of the culture medium, it is possible for the quantitative proportion of one or more of the cephaibols according to the invention to vary. Moreover, the synthesis of individual cephaibols can be controlled by the composition of the media, such that one or a number of the cephaibols are not produced at all or are produced in an amount below the detection limit of the microorganism.

The mixture preferably consists of 8 different, detectable cephaibols (cephaibols A, A1, B, C, D, E and also P and Q). The cephaibols A to E are preferably formed.

In addition to the cephaibols A1 and A to E (compounds of the formula I which carry phenylalaninol (Phe-ol16) as a characteristic element at the C terminus), compounds of the formula I that carry the aldehyde phenylalaninal (Phe-al16) instead of Phe-ol16 as the C terminal group are also formed in the culture medium of the *Acremonium tubakii* FH 1685 DSM 12774. As a rule, these are minority products to the cephaibols A–E and are obtained from the culture medium together with these.

The microorganism is cultured aerobically, i.e., for example, with shaking or stirring in shaker flasks or fermenters, and if appropriate, with introduction of air or oxygen.

It can be carried out in a temperature range from approximately 18 to 35° C., preferably at approximately 20 to 30° C., in particular at 22 to 28° C. The pH range should be from about 6 to about 8, preferably from about 6.5 to about 7.5. In general, the microorganism is cultured under these conditions over a period of about 24 to 300 hours, preferably about 36 to 140 hours.

Culturing is advantageously carried out in several stages, i.e., one or more precultures are first prepared in a liquid culture medium, which are then inoculated into the actual production medium, the main culture, for example, in the volume ratio 1:10. The preculture is obtained, for example, by inoculating a mycelium into a nutrient solution and allowing it to grow for approximately 36 to 120 hours, preferably 48 to 72 hours. The mycelium can be obtained, for example, by allowing the strain to grow for approximately 3 to 40 days, preferably 4 to 10 days, on a solid or liquid nutrient medium, for example, malt-yeast-agar or potato-dextrose-agar (standard medium for mold fungi, e.g., from Difco).

The course of the fermentation can be monitored by means of the pH of the cultures or of the mycelium volume and by chromatographic methods, such as, for example, thin-layer chromatography or high-pressure liquid chromatography, or testing of the biological activity. The cephaibols according to the invention are obtained both in the mycelium and in the culture filtrate, but the largest part is found in the mycelium.

The isolation procedure described below is used for the purification of the cephaibols according to the invention, preferably for the purification of the cephaibols A, A1, B, C and D.

The isolation or purification of the cephaibols according to the invention from the culture medium is carried out according to known methods taking into account the chemical, physical and biological properties of the natural substances. For testing the peptide active compound concentration in the culture medium or in the individual isolation steps, it is possible to use thin-layer chromatography, for example, on silica gel using isopropanol/25% strength $NH_3$ as an eluant or HPLC. Detection in the case of the thin-layer chromatographic separation can be carried out, for example, by means of staining reagents such as anisaldehyde/sulfuric acid, the amount of the substance formed expediently being compared with a calibration solution. The by-products of the formula I, in which R is a Phe-al radical, can optionally be separated from the respective cephaibol A–E by customary purification methods known to the person skilled in the art, for example, by chromatography or by recrystallization.

For the isolation of the cephaibols according to the invention, the mycelium is first separated from the culture medium by the customary processes and the cephaibols are then extracted from the cell mass using an optionally water-miscible organic solvent. The organic solvent phase contains the cephaibols according to the invention; they are optionally concentrated in vacuo and further purified as described below.

The culture filtrate is optionally combined with the concentrate of the mycelium extract and extracted with a suitable, water-immiscible organic solvent, for example, with n-butanol. The subsequently separated organic phase is optionally concentrated in vacuo. For the defatting of the product of value, it is possible to dilute the concentrate with a nonpolar solvent in which the cephaibols according to the invention are soluble to a very small extent, such as, for example, with hexane, petroleum ether, or diethyl ether. The cephaibols precipitate in this process and the lipophilic impurities remain dissolved and are removed by customary solid/liquid phase separations.

The precipitate, which contains all the cephaibols, is dissolved in 1/30 of the original volume of water/methanol. The precipitate dissolves completely into solution during the course of this and the solution is lyophilized. The lyophilizate, subsequently called the crude product, contains 5 to 50% of cephaibols and is employed for further isolation.

The further purification of one or more of the cephaibols according to the invention is carried out by chromatography on suitable materials, preferably, for example, on molecular sieves, on silica gel or alumina, on ion exchangers or on adsorber resins or on reversed phases (RP). Using this chromatography, the cephaibols are separated. The chromatography of the cephaibols is carried out with buffered aqueous solutions or mixtures of aqueous and organic solutions.

Mixtures of aqueous and organic solutions are understood as meaning all water-miscible organic solvents, preferably methanol or acetonitrile, in a concentration of 10 to 80% of solvent, preferably 40 to 60% of solvent, or otherwise all buffered aqueous solutions which are miscible with organic solvents.

The separation of the cephaibols on the basis of their differing polarity is carried out with the aid of reversed phase chromatography, for example, on MCI® (adsorber resin from Mitsubishi, Japan) or Amberlite XAD® (TOSO-HAAS), on further hydrophobic materials, such as, for example, on RP-8 or RP-18 phases. Moreover, the separation can be carried out with the aid of normal-phase chromatography, for example, on silica gel, alumina and the like.

The chromatography of the cephaibols is carried out with buffered or acidified aqueous solutions or mixtures of aqueous solutions with alcohols or other, water-miscible organic solvents. The organic solvents used are preferably propanol and acetonitrile.

Buffered or acidified aqueous solutions are understood as meaning, for example, water, phosphate buffer, ammonium acetate, citrate buffer in a concentration of 0.1 mM to 0.5 M, and formic acid, acetic acid, trifluoroacetic acid or all customary acids known to the person skilled in the art, preferably in a concentration of 0.01 to 1%. 0.1% is particularly preferred.

Chromatography is carried out using a gradient which begins with 100% water and ends with 100% solvent, preferably a linear gradient from 30 to 60% propanol or acetonitrile is employed.

Alternatively, it is also possible to carry out gel chromatography or chromatography on hydrophobic phases.

Gel chromatography is carried out on polyacrylamide or mixed polymer gels, such as, for example, Biogel-P 2® (Biorad) or Fractogel TSK HW 40® (Merck, Germany, Toso Haas, USA) or Sephadex® (Pharmacia, Sweden).

The sequence of the abovementioned chromatographies is reversible.

A further, very effective purification step for cephaibols is crystallization. The cephaibols crystallize readily from solutions in organic solvents and from mixtures of water with organic solvents. The crystallization is carried out in a manner known per se, for example, by concentrating or cooling saturated peptide active compound solutions.

The cephaibols according to the invention are stable in the solid state and in solutions in the pH range from about 3 to about 8, in particular from about 5 to about 7, and can thus be incorporated into customary pharmaceutical preparations.

Physiologically tolerable salts of compounds of the formula I or II are understood as meaning both their organic and inorganic salts, such as are described in Remington's Pharmaceutical Sciences ($17^{th}$ Edition, page 1418 (1985)). Because of their physical and chemical stability and solubility, sodium, potassium, calcium and ammonium salts, inter alia, are preferred for acidic groups; salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid, inter alia, are preferred for basic groups.

The present invention comprises all stereoisomeric forms of the compounds of the formula I or II. Asymmetric centers contained in the compounds of the formula II can all independently of one another have the S configuration or the R configuration. The invention includes all possible enantiomers and diastereomers, as well as mixtures of two or more stereoisomeric forms, for example, mixtures of enantiomers and/or diastereomers, in all ratios. Enantiomers are thus a subject of the invention in enantiomerically pure form, both as levorotatory and as dextrorotatory antipodes, in the form of racemates and in the form of mixtures of the two enantiomers in all ratios. In the presence of cis/trans isomerism, both the cis form and the trans form and mixtures of these forms in all ratios are a subject of the invention.

The present invention also comprises chemical equivalents of the compounds of the formula I or II. Equivalents of this type are, for example, esters, ethers, addition salts, complexes or otherwise partial hydrolysis products.

Because of their valuable pharmacological properties, the cephaibols according to the invention are suitable for use as pharmaceuticals in human and/or veterinary medicine. The substances according to the invention possess pharmacological activity, in particular as an antibiotic against parasites, particularly preferably against endo- and/or ectoparasites.

The present invention thus further relates to the use of the compounds of the formula I or II according to the invention as human or veterinary pharmaceuticals, in particular as chemotherapeutics against human- and/or animal-pathogenic endo-and/or ectoparasites. The mechanism of action of these peptide active compounds is unknown, but a significant, lethal effect against helminths and ectoparasites was detected.

The cephaibols according to the invention are suitable, for example, for the control of animal- and human-pathogenic trematodes (*Fasciola hepatica, Fasciolopsis buski, Fasciola gigantica, Fascioloides magna, Dicrocoelium dendriticum, Opistorchis felineus, Clonorchis sinensis, Paragonimus westermanni, Paragonimus kellikotti, Schistosoma haematobium, Schistosoma japonicum, Schistosoma mansoni*) and animal- and human-pathogenic nematodes which belong to the family of the Trichuridae, Trichinellidae, Strongyloididae, Ancylostomatidae, Strongylidae, Trichostrongylidae, Metastrongylidae, Oesophagostomatidae, Dictyocaulidae, Protostrongylidae, Angiostrongylidae, Oxyuridae, Ascaridae, Toxocaridae, Dracunculidae, Habronematidae and Filariidae; moreover, the cephaibols according to the invention are suitable for the control of animal- and human-pathogenic ectoparasites which belong to the arachnids class (family: Argasidae, Ixodidae, Dermanyssidae; Demodicidae, Sarcoptidae, Psoroptidae, Varroidae) and to the insects class, which comprise the order of the Phthiraptera (Anoplura, Mallophaga), Diptera and Siphonaptera.

In addition to the antibacterial action, the compounds according to the invention possess antimycotic, i.e., antifungal properties, including the phytopathogenic fungi.

In the case of parasites that have formed resistance to conventional agents, only novel agents possess a therapeutically adequate action. The cephaibols of the formula I or II according to the invention thus potentially have an excellent action even against these problem organisms.

Because of the antibacterial, antimycotic and antiprotozoal activity, the cephaibols according to the invention possess growth-promoting actions, which can be used to good effect in animal production. The improved feed utilization can be utilized in farm animals such as, for example, cattle, sheep, goats, pigs, horses or rabbits. For this, doses of 0.05–50 mg/kg/day are preferably used. The cephaibols in this case also bring about a decrease in the production of methane gas and an improvement in the feed utilization.

The invention also relates to pharmaceutical preparations that contain one or more of the cephaibols according to the invention. Use as a mixture with suitable excipients or carrier material is preferred. Carrier material which can be used in veterinary pharmaceuticals are the customary feedstuff mixtures or, in the case of humans, all pharmacologically tolerable carrier materials and/or excipients.

The invention also relates to a process for the production of a pharmaceutical according to the invention, which comprises bringing at least one of the compounds according to the invention into a suitable administration form using a pharmaceutically suitable and physiologically tolerable carrier and, if appropriate, further suitable active compounds, additives or excipients.

In general, the pharmaceuticals according to the invention are administered orally, locally, or parenterally, and, in principle rectal administration is also possible.

Suitable solid or liquid pharmaceutical preparation forms are, for example, granules, powders, tablets, coated tablets, (micro)capsules, suppositories, syrups, emulsions, suspensions, aerosols, drops or injectable solutions in ampoule form and also preparations with protracted release of active compound, in whose production vehicles and additives and/or excipients, such as disintegrants, binders, coating agents, swelling agents, glidants or lubricants, flavorings, sweeteners or solubilizers, are customarily used. Frequently used vehicles or excipients which may be mentioned are, for example, magnesium carbonate, titanium dioxide, lactose, mannitol, and other sugars, talc, lactoprotein, gelatin, starch, vitamins, cellulose and its derivatives, animal or vegetable oils, polyethylene glycols and solvents, such as, for example, sterile water, alcohols, glycerol, and polyhydric alcohols.

If appropriate, the dose units can be microencapsulated for oral administration in order to delay the release or to extend it over a longer period of time, such as, for example, by coating or embedding the active compound in particle form into suitable polymers, waxes, or the like.

The pharmaceutical preparations are preferably produced and administered in dose units, each unit containing as active constituent a specific dose of one or more compounds of the cephaibols according to the invention. In the case of solid dose units such as tablets, capsules and suppositories, this dose can be up to approximately 2000 mg, but preferably approximately 1 to 1000 mg, and in the case of injection solutions in ampoule form up to approximately 1000 mg, but preferably approximately 10 to 300 mg, per day.

The daily dose to be administered is dependent on the body weight, age, sex and condition of the mammal. Under certain circumstances, however, even higher or lower daily doses may be appropriate. The administration of the daily dose can be carried out either by single administration in the form of an individual dose unit or in a number of smaller dose units and by multiple administration of subdivided doses at specific intervals.

The pharmaceuticals according to the invention are produced by bringing one or more compounds of the cephaibols according to the invention into a suitable administration form using customary vehicles and, if appropriate, additives and/or excipients.

In principle, in the treatment of helminths and ectoparasites, a differentiation is to be made between therapeutic, meta- and prophylactic measures; these different treatment methods require specific, pharmaceutical formulations. Formulations of this type guarantee, for example, the continuous administration of subtherapeutic to therapeutic doses of anthelmintics or of ectoparasiticides, which are differentiated into "sustained-" and "pulse-release boli" according to their mode of release. The former are further differentiated into "slow-release boli", which are those with a decreasing release rate, and "continuous-release boli", which are those with a constant release mode. "Pulse-release boli", on the other hand, release all of the active compound within a few hours to days. In addition to the release technology, which also comprises the microencapsulation of active compounds and which enjoys increasing popularity in veterinary medicine, so-called "spot on" or "pour on" formulations are customary for external application to the animal. The administration of tablets, pastes, or injection solutions and the use of neckbands that contain medicaments against, for example, ectoparasites, are known in the prior art.

The invention is illustrated further in the following examples. Percentages relate to weight. Mixing ratios in liquids relate to volume, if no other details have been given.

EXAMPLES

Example 1

Preparation of a Glycerol Culture of *Acremonium tubakii* FH 1685 DSM 12774

100 ml of nutrient solution (malt extract 2.0%, yeast extract 0.2%, glucose 1.0%, $(NH_4)_2HPO_4$ 0.05%, pH 6.0) in a sterile 300 ml Erlenmeyer flask are inoculated with the strain *Acremonium tubakii* FH 1685 DSM 12774 and incubated on a rotating shaker for 7 days at 25° C. and 140 rpm. 1.5 ml of this culture are then diluted with 2.5 ml of 80% glycerol and stored at −20° C.

Example 2

Preparation of a Culture or a Preculture in the Erlenmeyer Flask of *Acremonium tubakii* FH 1685 DSM 12774

A sterile 300 ml Erlenmeyer flask containing 100 ml of the following nutrient solution: 30 g/l of sucrose, 5 g/l of yeast extract, 1 g/l of $K_2HPO_4$, 3 g/l of $NaNO_3$, 0.5 g/l of $MgSO_4 \times 7H_2O$, 0.01 g/l of $FeSO_4 \times 7H_2O$, 0.5 g/l of KCl and 1.0 ml of trace element solution (0.2 g/l of $ZnSO_4 \times 7H_2O$ and 0.7 g/l of $CuSO_4 \times 5H_2O$) is inoculated with a culture grown on a slant tube (same nutrient solution, but with 2% agar) or with 1 ml of a glycerol culture (see Example 1) and incubated on a shaker at 180 rpm and 30° C. The maximum production of one or more compounds of the cephaibols according to the invention is achieved after about 120 hours. For the inoculation of 10 and 200 liter fermenters, the 48 to 96 hour-old submersed culture (inoculation quantity about 10%) of the same nutrient solution suffices.

Example 3

Preparation of the Cephaibols

A 30-liter fermenter is operated under the following conditions:

| | |
|---|---|
| Nutrient medium: | 30 g/l of sucrose |
| | 5 g/l of yeast extract |
| | 3 g/l of $NaNO_3$ |
| | 0.5 g/l of KCl |
| | 0.5 g/l of $MgSO_4$ |
| | 0.1 g/l of $K_2HPO_4$ |
| | 10 μM $FeCl_3 \times 6H_2O$ |
| | 1 ml of trace element solution |
| | pH 6.5 (before sterilization) |
| Trace element solution: | 2 g/l of $ZnSO_4 \times 7H_2O$ and |
| | 0.7 g/l of $CuSO_4 \times 5H_2O$. |
| Incubation time: | 50 hours |
| Incubation temperature: | 25° C. |
| Stirrer speed: | 300 rpm |
| Aeration: | 15 liter $min^{-1}$ |

By repeated addition of ethanolic polyol solution, it is possible to suppress foam formation. The production maximum is achieved after about 96 to 120 hours.

Example 4

Isolation of the Cephaibol Mixture from the Culture Solution of *Acremonium tubakii* FH 1685 DSM 12774

After completion of the fermentation of *Acremonium tubakii* FH 1685 DSM 12774, the culture broth from three fermenters, obtained according to Example 3, (90 liters) is filtered with the addition of approximately 2% filter aid (e.g., Celite®) and the cell mass (6 liters) is extracted with 20 liters of methanol. The peptide active compound-containing, methanolic solution is freed from the mycelium by filtration and concentrated in vacuo. The concentrate is applied together with the culture filtrate (83 liters) to a previously prepared, 4 liter MCI gel, CHP20P column. This is eluted with a gradient of 0.1% trifluoroacetic acid in water to 0.1% trifluoroacetic acid in propan-2-ol. The flow through the column (12 liters per hour) is collected in fractions (2.5 liters each) and the fractions containing the peptide active compounds (21 to 24) are combined. Concentration in vacuo and freeze-drying afford 4 g of a pale brown powder.

Example 5

Enrichment of the Cephaibol Components by Gel Chromatography 4 g of the product obtained according to Example 4 are applied to a 3.9 liter capacity column packed with Fractogel® TSK MW40 s (width×height=10 cm×50 cm). The eluant methanol is pumped through the column at a flow rate of 50 ml per minute and the column efflux is collected in fractions (65 ml). The cephaibols are found mainly in fractions 28 to 33. They are combined and freed from the methanol in vacuo. They afford 1.3 g of peptide active compound mixture.

Example 6

Separation of the Cephaibol Components on Reverse-phase RP-18

A 500 ml capacity preparative HPLC column (5.1 cm (ID)×25 cm H) is packed with ®Nucleosil 100-7 C18 HD and the 1.3 g of the peptide active compound mixture obtained according to Example 5 are applied. Elution is carried out with 40% acetonitrile in 0.1% aqueous trifluoroacetic acid solution. The flow through the column is 50 ml/minute and fractions of a content of 125 ml each are collected. Cephaibol D is found in fraction 46, cephaibol C in fractions 49 and 50, cephaibol E in fraction 51, cephaibol A in fractions 60 to 64 and cephaibol B and A1 in fractions 66 and 67. Fraction 68 comprises a mixture of cephaibols. After concentrating in vacuo and freeze-drying, the following amounts are weighed out:

Cephaibol A: 520 mg, ESI+MS: 1671 Da $(M+H)^+$,

Cephaibol A1: 4 mg, ESI+MS: 1685 DA $(M+H)^+$

Cephaibol B: 38 mg, ESI+MS: 1685 Da $(M+H)^+$,

Cephaibol C: 195 mg, ESI+MS: 1657 Da $(M+H)^+$,

Cephaibol D: 16 mg, ESI+MS: 1643 Da $(M+H)^+$,

Cephaibol E: 76 mg, ESI+MS: 1657 Da $(M+H)^+$.

Example 7

Isolation of the Cephaibols P and Q

Fraction 68, obtained according to Example 6, is dissolved, after freeze drying (4.1 mg), in 20% acetonitrile in water and applied to a 250/10 Nucleosil C18 300-7® column. Elution is carried out with 0.005% ammonium acetate buffer in 40% acetonitrile. In addition to a little cephaibol B, 1 mg of cephaibol P and 1 mg of cephaibol Q are obtained after drying.

Cephaibol P: ESI+MS a molecular weight of 1873 $(M+H)^+$ is measured,

Cephaibol Q: ESI+MS a molecular weight of 1857 $(M+H)^+$ is measured.

Example 8

HPLC System for the Detection of the Cephaibols

The system described below allows the separation and quantification of the cephaibols in the crude mixture or in the culture filtrate; the retention times are between 7.0 minutes (cephaibol D) and 18.8 minutes (cephaibol A1).

| Eluant: | 0.1% trifluoroacetic acid in 40% acetonitrile. |
|---|---|
| Column: | Nucleosil 100$C_{18}$AB 250/4, Macherey-Nagel. |
| Flow: | 1.0 ml/min. |
| Detection: | Ultraviolet light absorption at 210 nm. |

Under the conditions indicated, the cephaibols have the following retention times:

Cephaibol A: 12.1 minutes,

Cephaibol A1: 18.8 minutes,

Cephaibol B: 16.0 minutes,

Cephaibol C: 9.0 minutes,

Cephaibol D: 7.1 minutes,

Cephaibol E: 7.3 minutes,

Cephaibol P: 17.3 minutes,

Cephaibol Q: 17.9 minutes.

Example 9

Characterization of Cephaibol A

10 μg of cephaibol A are hydrolyzed in constant-boiling hydrochloric acid and investigated in an amino acid analyzer. The following customary amino acids are found:

| Hydroxyproline | 11.5 nmol |
|---|---|
| Glutamic acid | 5.7 nmol |
| Proline | 5.5 nmol |
| Glycine | 5.5 nmol |
| Leucine | 5.6 nmol |
| Phenylalanine | 5.5 nmol |

The contents of the unusual amino acids aminoisobutyric acid and isovaline were not assessable.

Mass-spectrometric investigations using a Finnigan MAT LCQ ion-trap mass spectrometer with electron spray ionization (ESI+) afford the following data:

The ESI mass spectrum shows an intensive $MH^+$ at m/e 1670.7 and an $[M+Na]^+$ at m/e 1692.7 corresponding to a monoisotopic molecular weight of 1669.7, in good agreement with the calculated mass (for $C_{82}H_{127}N_{17}O_{20}$, monoisotopic) of 1669.9 Da. The MS/MS spectrum shows a fragmentation that is listed in bold in Table 9. The fragments printed in italics are calculated, but not observed fragments.

TABLE 9

MS/MS fragmentation of cephaibol A

| $B_1$ | 190.1 | $B_1$ | *212.1* | $A_1$ | *184.1* |
|---|---|---|---|---|---|
| $B_2$ | 275.1 | $B_2$ | *297.1* | $A_2$ | *269.1* |
| $B_3$ | 360.2 | $B_3$ | *382.2* | $A_3$ | *354.2* |
| $B_4$ | 445.2 | $B_4$ | *467.2* | $A_4$ | *439.2* |
| $B_5$ | 530.3 | $B_5$ | *552.3* | $A_5$ | *524.3* |
| $B_6$ | 587.3 | $B_6$ | *609.3* | $A_6$ | *581.3* |
| $B_7$ | 700.4 | $B_7$ | 722.4 | $A_7$ | 694.4 |
| $B_8$ | 799.5 | $B_8$ | 821.5 | $A_8$ | 793.5 |
| $B_9$ | 884.5 | $B_9$ | 906.5 | $A_9$ | 878.5 |
| $B_{10}$ | 997.6 | $B_{10}$ | 1019.6 | $A_{10}$ | *991.6* |
| $B_{11}$ | *1125.6* | $B_{11}$ | 1147.6 | $A_{11}$ | 1119.6 |
| $B_{12}$ | 1224.7 | $B_{12}$ | 1246.7 | $A_{12}$ | 1218.7 |
| $B_{13}$ | 1337.7 | $B_{13}$ | 1359.7 | $A_{13}$ | 1331.7 |
| $B_{14}$ | 1422.8 | $B_{14}$ | 1444.8 | $A_{14}$ | 1416.8 |
| $B_{15}$ | 1519.9 | $B_{15}$ | *1541.9* | $A_{15}$ | *1513.9* |

The protonated B fragmentation is listed in the first column—and in the second column the $(M+sodium)^+$-B fragmentation. The third column shows the A fragment series in the Na form.

The physicochemical and spectroscopic properties of the cephaibols according to the invention can be summarized as follows:

Cephaibol A (SEQ ID NO:1):

Appearance: soluble in polar organic solvents, but only slightly soluble in water; colorless substance. It is stable in neutral, mildly acidic and mildly alkaline medium.

Empirical formula: $C_{82}H_{127}N_{17}O_{20}$, structural formula:

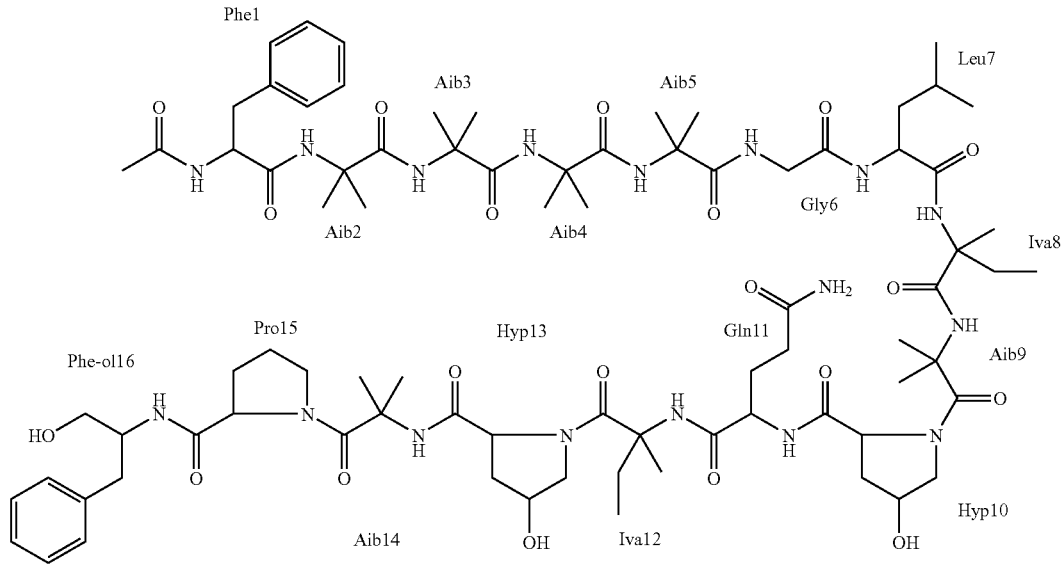

Cephaibol A molecular weight: 1671 Da,

UV absorption ($\lambda_{max}$): 258 nm, log ε: 2.62

NMR data: see Table 1

Cephaibol A1 (SEQ ID NO:8):

Appearance: soluble in polar organic solvents, but only slightly soluble in water; colorless substance. It is stable in neutral, mildly acidic and mildly alkaline medium.

Empirical formula: $C_{83}H_{129}N_{17}O_{20}$, structural formula:

molecular weight: 1685 Da,

UV data ($\lambda_{max}$): 258 nm, log ε: 2.62

NMR data: see Table 1a

Cephaibol B (SEQ ID NO:2):

Appearance: soluble in polar organic solvents, but only slightly soluble in water; colorless substance. It is stable in neutral, mildly acidic and mildly alkaline medium.

Empirical formula: $C_{83}H_{129}N_{17}O_{20}$, structural formula:

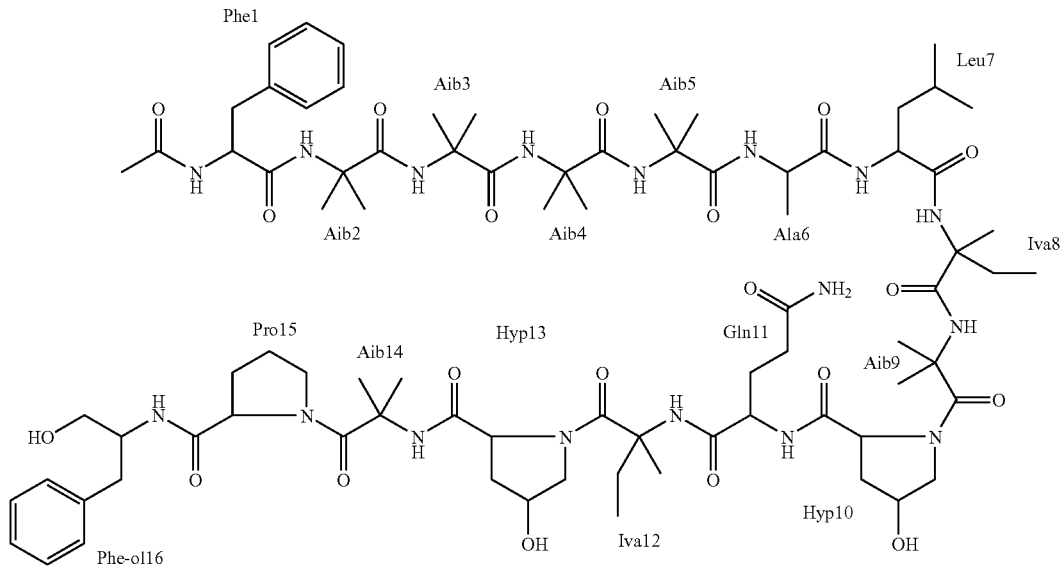

Cephaibol A1

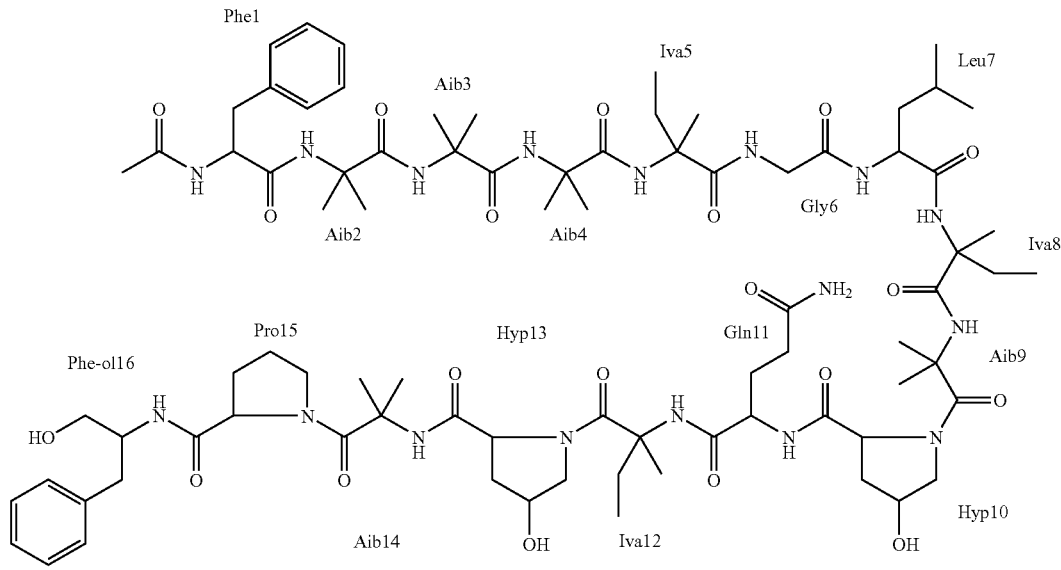

Cephaibol B molecular weight: 1685 Da,

UV absorption ($\lambda_{max}$): 258 nm, log ε: 2.62

NMR data: see Table 2.

Cephaibol C (SEQ ID NO:3):

Appearance: soluble in polar organic solvents, but only slightly soluble in water; colorless substance. It is stable in neutral, mildly acidic and mildly alkaline medium.

Empirical formula: $C_{81}H_{125}N_{17}O_{20}$, structural formula:

Molecular weight: 1657 Da,

UV absorption ($\lambda_{max}$): 258 nm, log ε: 2.62

NMR data: see Table 3.

Cephaibol D (SEQ ID NO:4):

Appearance: soluble in polar organic solvents, but only slightly soluble in water; colorless substance. It is stable in neutral, mildly acidic and mildly alkaline medium.

Empirical formula: $C_{80}H_{123}N_{17}O_{20}$, structural formula:

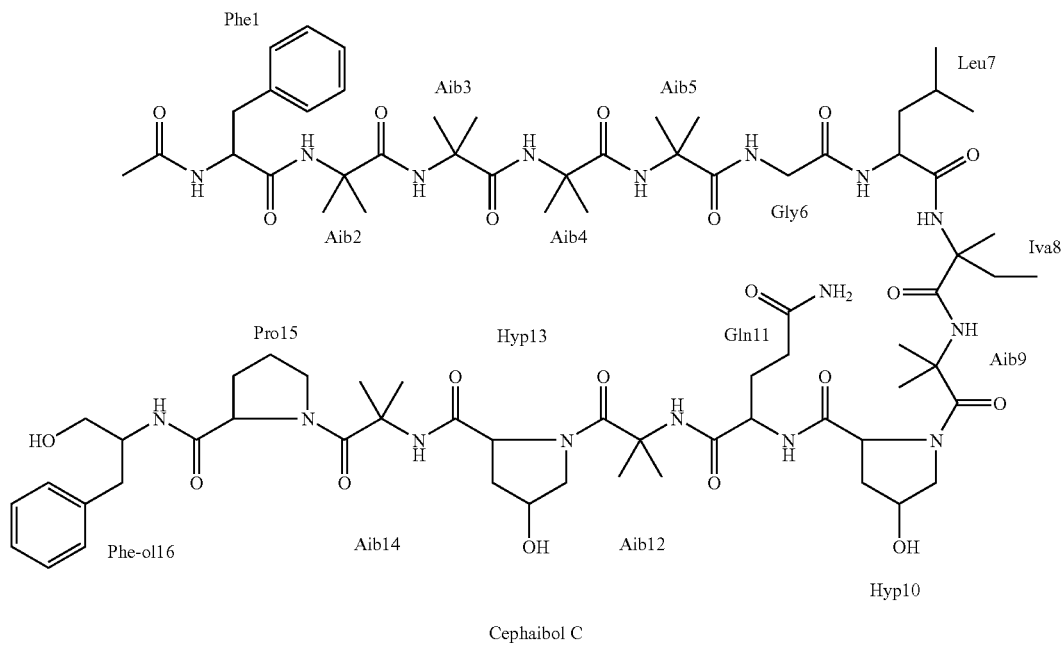

Cephaibol C

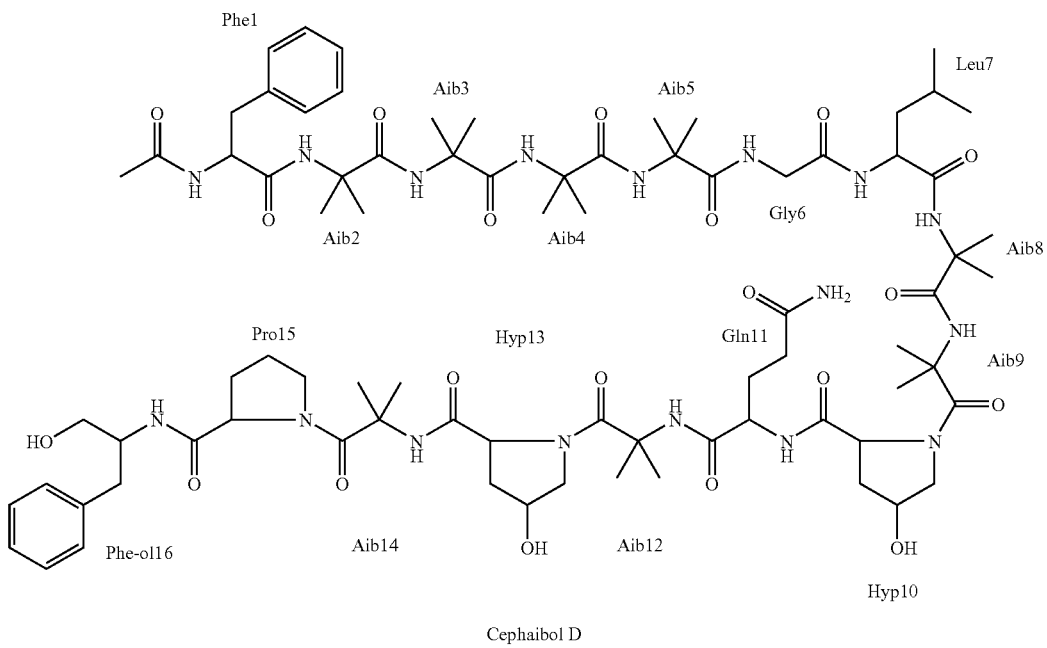

Cephaibol D molecular weight: 1643 Da,

UV absorption ($\lambda_{max}$): 258 nm, log ε: 2.62

NMR data: see Table 4.

Cephaibol E (SEQ ID NO:5):

Appearance: soluble in polar organic solvents, but only slightly soluble in water; colorless substance. It is stable in neutral, mildly acidic and mildly alkaline medium.

Empirical formula: $C_{81}H_{125}N_{17}O_{20}$, structural formula:

molecular weight: 1657 Da,

UV absorption ($\lambda_{max}$): 258 nm, log ε: 2.62

NMR data: see Table 5.

Cephaibol P (SEQ ID NO:6):

Appearance: soluble in polar organic solvents, but only slightly soluble in water; colorless substance. It is stable in neutral, mildly acidic and mildly alkaline medium.

Empirical formula: $C_{89}H_{137}N_{19}O_{25}$, structural formula:

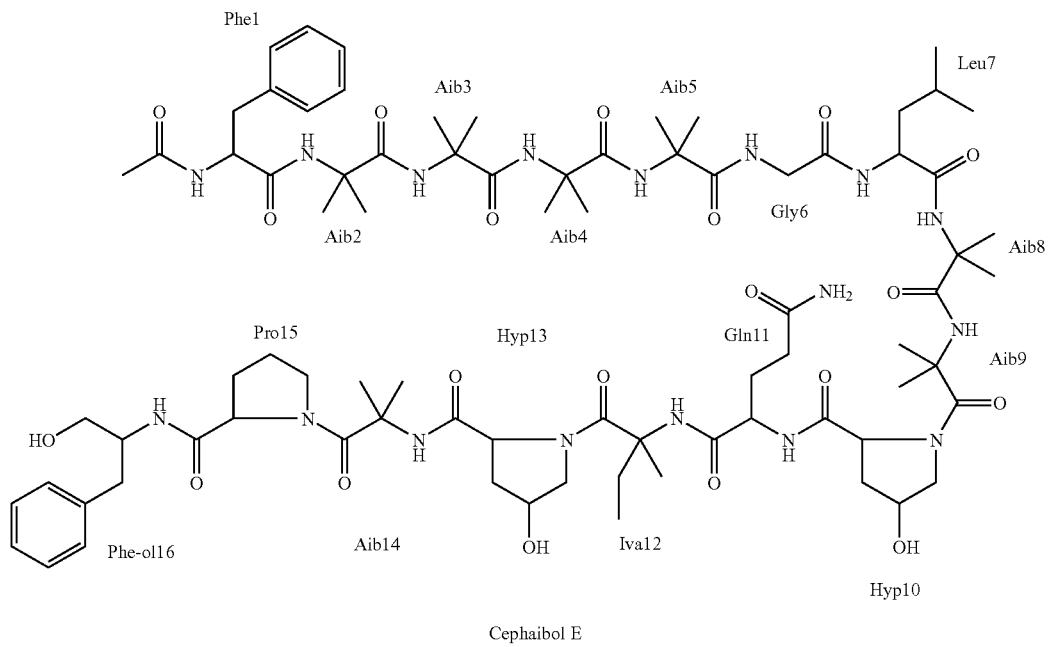

Cephaibol E

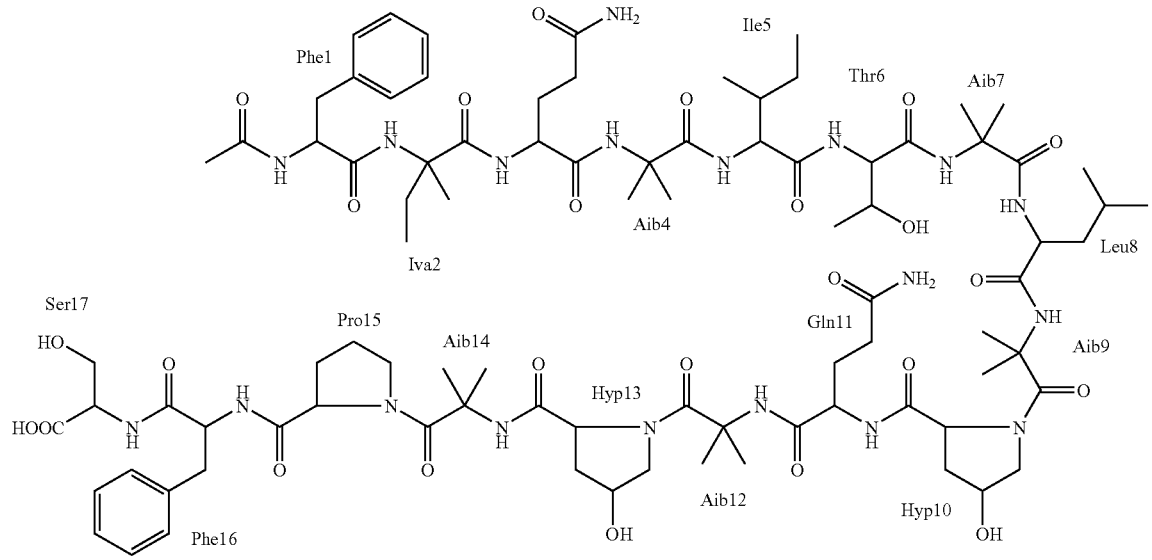

Cephaibol P molecular weight: 1873 Da,

NMR data: see Table 6.

Cephaibol Q (SEQ ID NO:7):

Appearance: soluble in polar organic solvents, but only slightly soluble in water; colorless substance. It is stable in neutral, mildly acidic and mildly alkaline medium.

Empirical formula: $C_{89}H_{137}N_{19}O_{24}$, structural formula:

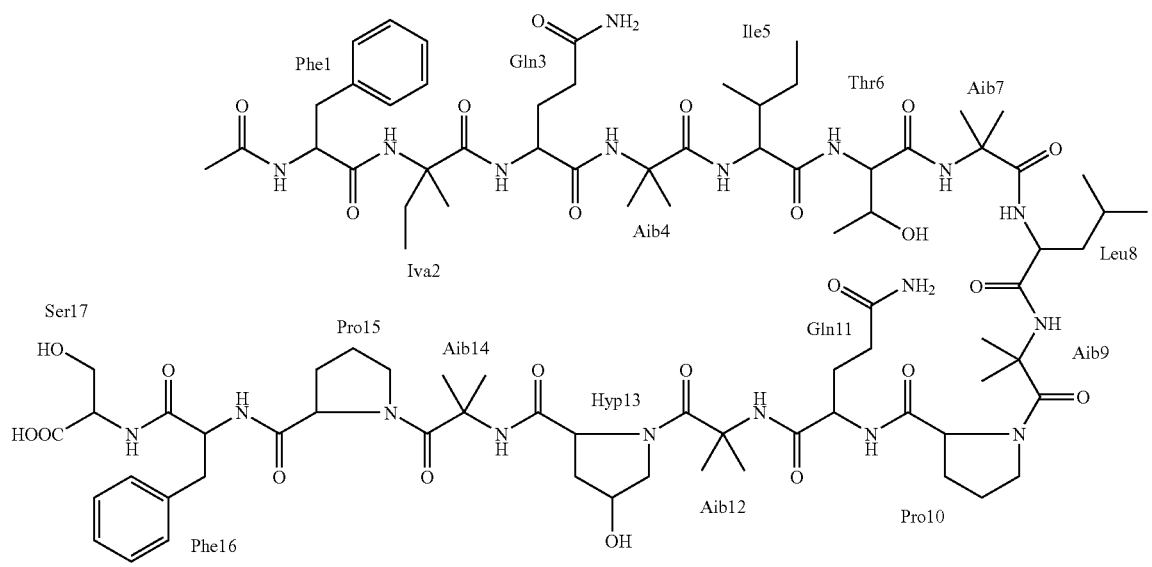

Cephaibol Q molecular weight: 1857.197 Da,

UV absorption ($\lambda_{max}$): 258 nm, log $\epsilon$: 2.62

NMR data: see Table 7.

TABLE 1

NMR data (chemical shifts) for cephaibol A in DMSO at 300° K.

| Proton/carbon | $^1H$ | $^{13}C$ |
|---|---|---|
| Ac-Me | 1.83 | 22.29 |
| Ac-C' | — | 170.37 |
| Phe1-NH | 8.29 | — |
| Phe1-α | 4.34 | 55.11 |
| Phe1-β | 2.97/2.83 | 36.37 |
| Phe1-γ | — | 137.37 |
| Phe1-δ | 7.29 | 129.16 |
| Phe1-ε | 7.29 | 128.09 |
| Phe1-ξ | 7.22 | 126.39 |
| Phe1-C' | — | 172.41 |
| Aib2-NH | 8.59 | — |
| Aib2-α | — | 55.77 |
| Aib2-β | 1.28 | 23.57 |
| Aib2-β' | 1.27 | 25.37 |
| Aib2-C' | — | 174.92 |
| Aib3-NH | 7.64 | — |
| Aib3-α | — | 55.86 |
| Aib3-β | 1.32 | 24.04 |
| Aib3-β' | 1.29 | 24.62 |
| Aib3-C' | — | 175.11 |
| Aib4-NH | 7.69 | — |

TABLE 1-continued

NMR data (chemical shifts) for cephaibol A in DMSO at 300° K.

| Proton/carbon | $^1H$ | $^{13}C$ |
|---|---|---|
| Aib4-α | — | 55.86 |
| Aib4-β | 1.39 | 24.99 |
| Aib4-β' | 1.38 | 24.55 |
| Aib4-C' | — | 175.62 |

TABLE 1-continued

NMR data (chemical shifts) for cephaibol A in DMSO at 300° K.

| Proton/carbon | $^1H$ | $^{13}C$ |
|---|---|---|
| Aib5-NH | 7.57 | — |
| Aib5-α | — | 55.92 |
| Aib5-β | 1.41 | 24.99 |
| Aib5-β' | 1.37 | 24.49 |
| Aib5-C' | — | 175.62 |
| Gly6-NH | 7.98 | — |
| Gly6-α | 3.76/3.64 | 43.43 |
| Gly6-C' | — | 170.69 |
| Leu7-NH | 7.74 | — |
| Leu7-α | 4.02 | 53.18 |
| Leu7-β | 1.70/1.53 | 39.40 |
| Leu7-γ | 1.69 | 24.13 |
| Leu7-δ | 0.92 | 22.62 |
| Leu7-δ' | 0.85 | 21.57 |
| Leu7-C' | — | 171.80 |
| Iva8-NH | 7.39 | — |
| Iva8-α | — | 59.34 |
| Iva8-β | 2.20/1.67 | 27.60 |
| Iva8-γ | 0.73 | 7.27 |
| Iva8-αMe | 1.27 | 21.93 |
| Iva8-C' | — | 176.07 |
| Aib9-NH | 7.57 | — |
| Aib9-α | — | 56.22 |
| Aib9-β | 1.48 | 23.17 |
| Aib9-β' | 1.37 | 25.72 |
| Aib9-C' | — | 173.44 |

TABLE 1-continued

NMR data (chemical shifts) for cephaibol A in DMSO at 300° K.

| Proton/carbon | ¹H | ¹³C |
| --- | --- | --- |
| Hyp10-α | 4.38 | 61.01 |
| Hyp10-β | 2.16/1.77 | 36.84 |
| Hyp10-γ | 4.29 | 68.95 |
| Hyp10-γOH | 5.11 | — |
| Hyp10-δ | 3.73/3.50 | 56.13 |
| Hyp10-C' | — | 171.80 |
| Gln11-NH | 7.89 | — |
| Gln11-α | 4.17 | 52.42 |
| Gln11-β | 2.16/1.86 | 26.66 |
| Gln11-γ | 2.09 | 31.44 |
| Gln11-δ | — | 173.08 |
| Gln11-ε-NH₂ | 7.19/6.70 | — |
| Gln11-C' | — | 172.13 |
| Iva12-NH | 7.47 | — |
| Iva12-α | — | 58.48 |
| Iva12-β | 2.15/1.78 | 28.06 |
| Iva12-γ | 0.74 | 6.97 |
| Iva12-αMe | 1.41 | 20.36 |
| Iva12-C' | — | 172.83 |
| Hyp13-α | 4.53 | 60.55 |
| Hyp13-β | 2.17/1.67 | 37.33 |
| Hyp13-γ | 4.21 | 69.04 |
| Hyp13-γOH | 5.09 | — |
| Hyp13-δ | 3.67/3.37 | 56.46 |
| Hyp13-C' | — | 172.83 |
| Aib14-NH | 7.94 | — |
| Aib14-α | — | 55.65 |
| Aib14-β | 1.40 | 23.50 |
| Aib14-β' | 1.33 | 25.66 |
| Aib14-C' | — | 171.73 |
| Pro15-α | 4.13 | 61.79 |
| Pro15-β | 1.83/1.16 | 28.34 |
| Pro15-γ | 1.58/1.48 | 24.83 |
| Pro15-δ | 3.79/3.50 | 47.36 |
| Pro15-C' | — | 170.69 |
| Phe16-NH | 7.15 | — |
| Phe16-α | 3.84 | 52.60 |
| Phe16-β | 2.99/2.57 | 36.37 |
| Phe16-γ | — | 139.47 |
| Phe16-δ | 7.25 | 129.33 |
| Phe16-ε | 7.24 | 127.93 |
| Phe16-ξ | 7.13 | 125.65 |
| Phe16-CH₂—OH | 3.39/3.24 | 63.42 |
| Phe16-CH₂—OH | 4.57 | — |

TABLE 1a

NMR data (chemical shifts) for cephaibol A1 in DMSO at 300° K.

| Proton/carbon | ¹H | ¹³C |
| --- | --- | --- |
| Ac-Me | 1.83 | 22.34 |
| Ac-C' | — | 170.18 |
| Phe1-NH | 8.22 | — |
| Phe1-α | 4.39 | 54.88 |
| Phe1-β | 3.04/2.83 | 36.41 |
| Phe1-γ | — | 137.53 |
| Phe1-δ | 7.29 | 129.10 |
| Phe1-ε | 7.29 | 128.04 |
| Phe1-ξ | 7.21 | 126.32 |
| Phe1-C' | — | 172.09 |
| Aib2-NH | 8.50 | — |
| Aib2-α | — | 55.73 |
| Aib2-β | 1.31 | 24.39 |
| Aib2-β' | 1.30 | 24.60 |
| Aib2-C' | — | 174.55 |
| Aib3-NH | 7.73 | — |
| Aib3-α | — | 55.73 |
| Aib3-β | 1.32 | 25.41 |
| Aib3-β' | 1.29 | 23.12 |
| Aib3-C' | — | 175.38 |

TABLE 1a-continued

NMR data (chemical shifts) for cephaibol A1 in DMSO at 300° K.

| Proton/carbon | ¹H | ¹³C |
| --- | --- | --- |
| Aib4-NH | 7.80 | — |
| Aib4-α | — | 55.82 |
| Aib4-β | 1.35 | 25.92 |
| Aib4-β' | 1.34 | 23.12 |
| Aib4-C' | — | 175.60 |
| Aib5-NH | 7.66 | — |
| Aib5-α | — | 55.70 |
| Aib5-β | 1.40 | 26.24 |
| Aib5-β' | 1.39 | 23.20 |
| Aib5-C' | — | 175.68 |
| Ala6-NH | 7.70 | — |
| Ala6-α | 4.01 | 50.69 |
| Ala6-β | 1.38 | 16.47 |
| Ala6-C' | — | 174.55 |
| Leu7-NH | 7.67 | — |
| Leu7-α | 3.96 | 53.49 |
| Leu7-β | 1.67/1.57 | 39.29 |
| Leu7-γ | 1.72 | 24.18 |
| Leu7-δ | 0.90 | 22.58 |
| Leu7-δ' | 0.84 | 21.29 |
| Leu7-C' | — | 171.81 |
| Iva8-NH | 7.18 | — |
| Iva8-α | — | 59.29 |
| Iva8-β | 2.31/1.65 | 26.62 |
| Iva8-γ | 0.70 | 7.15 |
| Iva8-αMe | 1.28 | 22.37 |
| Iva8-C' | — | 176.12 |
| Aib9-NH | 7.46 | — |
| Aib9-α | — | 56.16 |
| Aib9-β | 1.50 | 23.12 |
| Aib9-β' | 1.38 | 25.65 |
| Aib9-C' | — | 173.39 |
| Hyp10-α | 4.39 | 60.99 |
| Hyp10-β | 2.17/1.78 | 36.95 |
| Hyp10-γ | 4.29 | 68.94 |
| Hyp10-γOH | 5.11 | — |
| Hyp10-δ | 3.74/3.55 | 56.27 |
| Hyp10-C' | — | 171.92 |
| Gln11-NH | 7.91 | — |
| Gln11-α | 4.17 | 52.37 |
| Gln11-β | 2.15/1.86 | 26.71 |
| Gln11-γ | 2.10 | 31.37 |
| Gln11-δ | — | 173.03 |
| Gln11-ε-NH₂ | 7.19/6.70 | — |
| Gln11-C' | — | 172.15 |
| Iva12-NH | 7.47 | — |
| Iva12-α | — | 58.47 |
| Iva12-β | 2.15/1.78 | 28.04 |
| Iva12-γ | 0.74 | 6.94 |
| Iva12-αMe | 1.42 | 20.34 |
| Iva12-C' | — | 172.82 |
| Hyp13-α | 4.54 | 60.54 |
| Hyp13-β | 2.17/1.68 | 37.33 |
| Hyp13-γ | 4.22 | 69.03 |
| Hyp13-γOH | 5.08 | — |
| Hyp13-δ | 3.68/3.38 | 56.45 |
| Hyp13-C' | — | 172.82 |
| Aib14-NH | 7.95 | — |
| Aib14-α | — | 55.63 |
| Aib14-β | 1.39 | 23.50 |
| Aib14-β' | 1.33 | 25.65 |
| Aib14-C' | — | 171.71 |
| Pro15-α | 4.13 | 61.78 |
| Pro15-β | 1.85/1.17 | 28.33 |
| Pro15-γ | 1.59/1.48 | 24.82 |
| Pro15-δ | 3.79/3.51 | 47.35 |
| Pro15-C' | — | 170.68 |
| Phe16-NH | 7.16 | — |
| Phe16-α | 3.84 | 52.59 |
| Phe16-β | 2.99/2.58 | 36.41 |
| Phe16-γ | — | 139.46 |
| Phe16-δ | 7.25 | 129.32 |
| Phe16-ε | 7.25 | 127.92 |
| Phe16-ξ | 7.14 | 125.64 |

TABLE 1a-continued

NMR data (chemical shifts) for cephaibol A1 in DMSO at 300° K.

| Proton/carbon | $^1$H | $^{13}$C |
|---|---|---|
| Phe16-CH$_2$—OH | 3.39/3.25 | 63.41 |
| Phe16-CH$_2$—OH | 4.56 | — | a) A resolution of signals is observed in the $^{13}$C spectrum.

TABLE 2

NMR data (chemical shifts) for cephaibol B in DMSO at 300° K.

| Proton/carbon | $^1$H | $^{13}$C |
|---|---|---|
| Ac-Me | 1.84 | 22.28 |
| Ac-C' | — | 170.37 |
| Phe1-NH | 8.28 | — |
| Phe1-α | 4.33 | 55.14 |
| Phe1-β | 2.97/2.83 | 36.32 |
| Phe1-γ | — | 137.36 |
| Phe1-δ | 7.29 | 129.14 |
| Phe1-ε | 7.29 | 128.05 |
| Phe1-ξ | 7.22 | 126.37 |
| Phe1-C' | — | 172.40 |
| Aib2-NH | 8.58 | — |
| Aib2-α | — | 55.79 |
| Aib2-β | 1.28 | 23.69 |
| Aib2-β' | 1.27 | 25.24 |
| Aib2-C' | — | 174.81 |
| Aib3-NH | 7.62 | — |
| Aib3-α | — | 55.84 |
| Aib3-β | 1.32 | 24.10 |
| Aib3-β' | 1.29 | 24.60 |
| Aib3-C' | — | 175.10 |
| Aib4-NH | 7.73 | — |
| Aib4-α | — | 55.96 |
| Aib4-β | 1.38 | 24.82 |
| Aib4-β' | 1.38 | 24.82 |
| Aib4-C' | — | 175.45 |
| Iva5-NH | 7.49 | — |
| Iva5-α | — | 58.98 |
| Iva5-β | 1.99/1.70 | ~28.4(broad) |
| Iva5-γ | 0.80 | 7.49 |
| Iva5-αMe | 1.35 | 21.23 |
| Iva5-C' | — | 175.56 |
| Gly6-NH | 7.95 | — |
| Gly6-α | 3.77/3.64 | 43.34 |
| Gly6-C' | — | 170.67 |
| Leu7-NH | 7.74 | — |
| Leu7-α | 4.02 | 53.06 |
| Leu7-β | 1.69/1.53 | 39.40 |
| Leu7-γ | 1.69 | 24.10 |
| Leu7-δ | 0.92 | 22.63 |
| Leu7-δ' | 0.85 | 21.57 |
| Leu7-C' | — | 171.71 |
| Iva8-NH | 7.41 | — |
| Iva8-α | — | 59.35 |
| Iva8-β | 2.17/1.67 | 27.89 |
| Iva8-γ | 0.74 | 7.32 |
| Iva8-αMe | 1.27 | 21.77 |
| Iva8-C' | — | 176.08 |
| Aib9-NH | 7.58 | — |
| Aib9-α | — | 56.21 |
| Aib9-β | 1.48 | 23.15 |
| Aib9-β' | 1.36 | 25.75 |
| Aib9-C' | — | 173.44 |
| Hyp10-α | 4.39 | 60.99 |
| Hyp10-β | 2.16/1.78 | 36.83, 36.77[a)] |
| Hyp10-γ | 4.28 | 68.94, 68.84[a)] |
| Hyp10-γOH | 5.11 | — |
| Hyp10-δ | 3.73/3.50 | 56.09 |
| Hyp10-C' | — | 171.77 |
| Gln11-NH | 7.88 | — |
| Gln11-α | 4.17 | 52.42 |
| Gln11-β | 2.15/1.87 | 26.66 |

TABLE 2-continued

NMR data (chemical shifts) for cephaibol B in DMSO at 300° K.

| Proton/carbon | $^1$H | $^{13}$C |
|---|---|---|
| Gln11-γ | 2.10 | 31.42 |
| Gln11-δ | — | 173.00 |
| Gln11-ε-NH$_2$ | 7.18/6.70 | — |
| Gln11-C' | — | 172.11 |
| Iva12-NH | 7.46 | — |
| Iva12-α | — | 58.47 |
| Iva12-β | 2.15/1.77 | 28.06 |
| Iva12-γ | 0.74 | 6.97 |
| Iva12-αMe | 1.42 | 20.35 |
| Iva12-C' | — | 172.81 |
| Hyp13-α | 4.53 | 60.55 |
| Hyp13-β | 2.18/1.68 | 37.32, 37.26[a)] |
| Hyp13-γ | 4.21 | 69.03, 68.94[a)] |
| Hyp13-γOH | 5.08 | — |
| Hyp13-δ | 3.67/3.37 | 56.40 |
| Hyp13-C' | — | 172.81 |
| Aib14-NH | 7.94 | — |
| Aib14-α | — | 55.63 |
| Aib14-β | 1.40 | 23.49 |
| Aib14-β' | 1.33 | 25.65 |
| Aib14-C' | — | 171.71 |
| Pro15-α | 4.13 | 61.78 |
| Pro15-β | 1.83/1.16 | 28.33 |
| Pro15-γ | 1.58/1.47 | 24.82 |
| Pro15-δ | 3.79/3.50 | 47.35 |
| Pro15-C' | — | 170.67 |
| Phe16-NH | 7.15 | — |
| Phe16-α | 3.83 | 52.59, 52.56[a)] |
| Phe16-β | 2.99/2.57 | 36.37 |
| Phe16-γ | — | 139.46 |
| Phe16-δ | 7.25 | 129.32 |
| Phe16-ε | 7.25 | 127.91 |
| Phe16-ξ | 7.14 | 125.63 |
| Phe16-CH$_2$—OH | 3.39/3.24 | 63.42, 63.30[a)] |
| Phe16-CH$_2$—OH | 4.57 | — | a) A resolution of signals is observed in the $^{13}$C spectrum.

TABLE 3

NMR data (chemical shifts) for cephaibol C in DMSO at 300° K.

| Proton/carbon | $^1$H | $^{13}$C |
|---|---|---|
| Ac-Me | 1.83 | 22.23 |
| Ac-C' | — | 170.27 |
| Phe1-NH | 8.27 | — |
| Phe1-α | 4.34 | 54.99 |
| Phe1-β | 2.97/2.83 | 36.34 |
| Phe1-γ | — | 137.35 |
| Phe1-δ | 7.29 | 129.14 |
| Phe1-ε | 7.29 | 128.05 |
| Phe1-ξ | 7.22 | 126.38 |
| Phe1-C' | — | 172.39 |
| Aib2-NH | 8.58 | — |
| Aib2-α | — | 55.75 |
| Aib2-β | 1.28 | 23.51 |
| Aib2-β' | 1.27 | 25.34 |
| Aib2-C' | — | 174.81 |
| Aib3-NH | 7.63 | — |
| Aib3-α | — | 55.87 |
| Aib3-β | 1.32 | 23.97 |
| Aib3-β' | 1.29 | 24.55 |
| Aib3-C' | — | 175.08 |
| Aib4-NH | 7.69 | — |
| Aib4-α | — | 55.87 |
| Aib4-β | 1.38 | 24.85 |
| Aib4-β' | 1.38 | 24.55 |
| Aib4-C' | — | 175.62 |
| Aib5-NH | 7.56 | — |
| Aib5-α | — | 55.87 |
| Aib5-β | 1.41 | 24.85 |
| Aib5-β' | 1.37 | 24.55 |

TABLE 3-continued

NMR data (chemical shifts) for cephaibol C in DMSO at 300° K.

| Proton/carbon | $^1$H | $^{13}$C |
|---|---|---|
| Aib5-C' | — | 175.54 |
| Gly6-NH | 7.97 | — |
| Gly6-α | 3.76/3.63 | 43.35 |
| Gly6-C' | — | 170.63 |
| Leu7-NH | 7.72 | — |
| Leu7-α | 4.03 | 53.04 |
| Leu7-β | 1.69/1.51 | 39.41 |
| Leu7-γ | 1.69 | 24.11 |
| Leu7-δ | 0.91 | 22.60 |
| Leu7-δ' | 0.85 | 21.57 |
| Leu7-C' | — | 171.74 |
| Iva8-NH | 7.43 | — |
| Iva8-α | — | 59.34 |
| Iva8-β | 2.17/1.69 | 27.87 |
| Iva8-γ | 0.74 | 7.31 |
| Iva8-αMe | 1.29 | 21.87 |
| Iva8-C' | — | 176.04 |
| Aib9-NH | 7.54 | — |
| Aib9-α | — | 56.21 |
| Aib9-β | 1.48 | 23.23 |
| Aib9-β' | 1.36 | 25.49 |
| Aib9-C' | — | 173.59 |
| Hyp10-α | 4.39 | 61.12 |
| Hyp10-β | 2.16/1.77 | 36.75 |
| Hyp10-γ | 4.20 | 68.93 |
| Hyp10-γOH | broad | — |
| Hyp10-δ | 3.71/3.50 | 56.21 |
| Hyp10-C' | — | 171.74 |
| Gln11-NH | 7.80 | — |
| Gln11-α | 4.22 | 51.95 |
| Gln11-β | 2.18/1.83 | 26.17 |
| Gln11-γ | 2.09 | 31.23 |
| Gln11-δ | — | 173.10 |
| Gln11-ε-NH$_2$ | 7.18/6.69 | — |
| Gln11-C' | — | 172.02 |
| Aib12-NH | 7.75 | — |
| Aib12-α | — | 55.87 |
| Aib12-β | 1.50 | 23.80 |
| Aib12-β' | 1.38 | 25.73 |
| Aib12-C' | — | 172.26 |
| Hyp13-α | 4.51 | 60.54 |
| Hyp13-β | 2.16/1.69 | 37.22 |
| Hyp13-γ | 4.21 | 68.99 |
| Hyp13-γOH | broad | — |
| Hyp13-δ | 3.67/3.34 | 56.32 |
| Hyp13-C' | — | 172.70 |
| Aib14-NH | 7.95 | — |
| Aib14-α | — | 55.65 |
| Aib14-β | 1.41 | 23.41 |
| Aib14-β' | 1.34 | 25.58 |
| Aib14-C' | — | 171.70 |
| Pro15-α | 4.13 | 61.77 |
| Pro15-β | 1.84/1.16 | 28.34 |
| Pro15-γ | 1.58/1.49 | 24.55 |
| Pro15-δ | 3.80/3.51 | 47.36 |
| Pro15-C' | — | 170.63 |
| Phe16-NH | 7.14 | — |
| Phe16-α | 3.83 | 52.46 |
| Phe16-β | 2.98/2.57 | 36.34 |
| Phe16-γ | — | 139.46 |
| Phe16-δ | 7.25 | 129.30 |
| Phe16-ε | 7.25 | 127.90 |
| Phe16-ξ | 7.13 | 125.63 |
| Phe16-CH$_2$—OH | 3.38/3.24 | 63.32 |
| Phe16-CH$_2$—OH | broad | — |

TABLE 4

NMR data (chemical shifts) for cephaibol D in DMSO at 300° K.

| Proton/carbon | $^1$H | $^{13}$C |
|---|---|---|
| Ac-Me | 1.83 | 22.26 |
| Ac-C' | — | 170.27 |
| Phe1-NH | 8.28 | — |
| Phe1-α | 4.34 | 55.05 |
| Phe1-β | 2.97/2.83 | 36.34 |
| Phe1-γ | — | 137.35 |
| Phe1-δ | 7.29 | 129.14 |
| Phe1-ε | 7.29 | 128.05 |
| Phe1-ξ | 7.22 | 126.38 |
| Phe1-C' | — | 172.40 |
| Aib2-NH | 8.59 | — |
| Aib2-α | — | 55.76 |
| Aib2-β | 1.28 | 23.47 |
| Aib2-β' | 1.27 | 25.45 |
| Aib2-C' | — | 174.89 |
| Aib3-NH | 7.62 | — |
| Aib3-α | — | 55.87 |
| Aib3-β | 1.32 | 23.98 |
| Aib3-β' | 1.29 | 24.84 |
| Aib3-C' | — | 175.04 |
| Aib4-NH | 7.69 | — |
| Aib4-α | — | 55.87 |
| Aib4-β | 1.38 | 25.02 |
| Aib4-β' | 1.37 | 24.48 |
| Aib4-C' | — | 175.59 |
| Aib5-NH | 7.57 | — |
| Aib5-α | — | 55.87 |
| Aib5-β | 1.40 | 24.84 |
| Aib5-β' | 1.38 | 24.73 |
| Aib5-C' | — | 175.51 |
| Gly6-NH | 7.98 | — |
| Gly6-α | 3.74/3.63 | 43.28 |
| Gly6-C' | — | 170.35 |
| Leu7-NH | 7.66 | — |
| Leu7-α | 4.05 | 52.56 |
| Leu7-β | 1.66/1.52 | 39.25 |
| Leu7-γ | 1.66 | 24.07 |
| Leu7-δ | 0.91 | 22.67 |
| Leu7-δ' | 0.85 | 21.64 |
| Leu7-C' | — | 171.60 |
| Aib8-NH | 7.78 | — |
| Aib8-α | — | 56.15 |
| Aib8-β | 1.45 | 25.45 |
| Aib8-β' | 1.35 | 25.02 |
| Aib8-C' | — | 175.80 |
| Aib9-NH | 7.52 | — |
| Aib9-α | — | 56.22 |
| Aib9-β | 1.46 | 23.33 |
| Aib9-β' | 1.34 | 25.45 |
| Aib9-C' | — | 173.64 |
| Hyp10-α | 4.38 | 61.09 |
| Hyp10-β | 2.15/1.78 | 36.58 |
| Hyp10-γ | 4.29 | 69.01 |
| Hyp10-γOH | broad | — |
| Hyp10-δ | 3.75/3.46 | 56.06 |
| Hyp10-C' | — | 171.67 |
| Gln11-NH | 7.77 | — |
| Gln11-α | 4.22 | 51.96 |
| Gln11-β | 2.18/1.84 | 26.16 |
| Gln11-γ | 2.09 | 31.33 |
| Gln11-δ | — | 173.10 |
| Gln11-ε-NH$_2$ | 7.18/6.68 | — |
| Gln11-C' | — | 172.03 |
| Aib12-NH | 7.76 | — |
| Aib12-α | — | 55.87 |
| Aib12-β | 1.50 | 23.81 |
| Aib12-β' | 1.38 | 25.76 |
| Aib12-C' | — | 172.27 |
| Hyp13-α | 4.51 | 60.54 |
| Hyp13-β | 2.16/1.70 | 37.25 |
| Hyp13-γ | 4.22 | 69.01 |
| Hyp13-γOH | broad | — |
| Hyp13-δ | 3.67/3.34 | 56.34 |
| Hyp13-C' | — | 172.75 |
| Aib14-NH | 7.95 | — |

TABLE 4-continued

NMR data (chemical shifts) for cephaibol D in DMSO at 300° K.

| Proton/carbon | $^1$H | $^{13}$C |
|---|---|---|
| Aib14-α | — | 55.66 |
| Aib14-β | 1.41 | 23.47 |
| Aib14-β' | 1.34 | 25.60 |
| Aib14-C' | — | 171.73 |
| Pro15-α | 4.13 | 61.77 |
| Pro15-β | 1.84/1.117 | 28.35 |
| Pro15-γ | 1.58/1.49 | 24.84 |
| Pro15-δ | 3.80/3.52 | 47.36 |
| Pro15-C' | — | 170.69 |
| Phe16-NH | 7.14 | — |
| Phe16-α | 3.84 | 52.47 |
| Phe16-β | 2.98/2.58 | 36.34 |
| Phe16-γ | — | 139.46 |
| Phe16-δ | 7.25 | 129.31 |
| Phe16-ε | 7.25 | 127.90 |
| Phe16-ξ | 7.13 | 125.63 |
| Phe16-CH$_2$—OH | 3.39/3.24 | 63.34 |
| Phe16-CH$_2$—OH | broad | — |

TABLE 5

NMR data (chemical shifts) for cephaibol E in DMSO at 300° K.

| Proton/carbon | $^1$H | $^{13}$C |
|---|---|---|
| Ac-Me | 1.83 | 22.27 |
| Ac-C' | — | 170.36 |
| Phe1-NH | 8.28 | — |
| Phe1-α | 4.34 | 55.10 |
| Phe1-β | 2.98/2.84 | 36.35 |
| Phe1-γ | — | 137.36 |
| Phe1-δ | 7.29 | 129.15 |
| Phe1-ε | 7.29 | 128.06 |
| Phe1-ξ | 7.23 | 126.39 |
| Phe1-C' | — | 172.42 |
| Aib2-NH | 8.58 | — |
| Aib2-α | — | 55.76 |
| Aib2-β | 1.28 | 25.39 |
| Aib2-β' | 1.27 | 23.51 |
| Aib2-C' | — | 174.90 |
| Aib3-NH | 7.62 | — |
| Aib3-α | — | 55.87 |
| Aib3-β | 1.32 | 24.08 |
| Aib3-β' | 1.29 | 24.63 |
| Aib3-C' | — | 175.06 |
| Aib4-NH | 7.69 | — |
| Aib4-α | — | 55.87 |
| Aib4-β | 1.38 | 25.14 |
| Aib4-β' | 1.38 | 24.94 |
| Aib4-C' | — | 175.60 |
| Aib5-NH | 7.58 | — |
| Aib5-α | — | 55.87 |
| Aib5-β | 1.40 | 24.94 |
| Aib5-β' | 1.37 | 24.53 |
| Aib5-C' | — | 175.64 |
| Gly6-NH | 7.99 | — |
| Gly6-α | 3.74/3.64 | 43.35 |
| Gly6-C' | — | 170.43 |
| Leu7-NH | 7.68 | — |
| Leu7-α | 4.04 | 52.73 |
| Leu7-β | 1.67/1.54 | 39.24 |
| Leu7-γ | 1.67 | 24.08 |
| Leu7-δ | 0.91 | 22.67 |
| Leu7-δ' | 0.86 | 21.64 |
| Leu7-C' | — | 171.71 |
| Aib8-NH | 7.72 | — |
| Aib8-α | — | 56.18 |
| Aib8-β | 1.45 | 25.26 |
| Aib8-β' | 1.34 | 25.66 |
| Aib8-C' | — | 175.84 |
| Aib9-NH | 7.54 | — |
| Aib9-α | — | 56.22 |

TABLE 5-continued

NMR data (chemical shifts) for cephaibol E in DMSO at 300° K.

| Proton/carbon | $^1$H | $^{13}$C |
|---|---|---|
| Aib9-β | 1.46 | 23.26 |
| Aib9-β' | 1.34 | 25.66 |
| Aib9-C' | — | 173.48 |
| Hyp10-α | 4.38 | 60.95 |
| Hyp10-β | 2.16/1.79 | 36.71 |
| Hyp10-γ | 4.29 | 68.95 |
| Hyp10-γOH | broad | — |
| Hyp10-δ | 3.77/3.48 | 56.00 |
| Hyp10-C' | — | 171.75 |
| Gln11-NH | 7.85 | — |
| Gln11-α | 4.17 | 52.48 |
| Gln11-β | 2.16/1.89 | 26.63 |
| Gln11-γ | 2.11 | 31.49 |
| Gln11-δ | — | 173.08 |
| Gln11-ε-NH$_2$ | 7.19/6.69 | — |
| Gln11-C' | — | 172.13 |
| Iva12-NH | 7.47 | — |
| Iva12-α | — | 58.47 |
| Iva12-β | 2.15/1.78 | 28.09 |
| Iva12-γ | 0.75 | 7.01 |
| Iva12-αMe | 1.41 | 20.37 |
| Iva12-C' | — | 172.83 |
| Hyp13-α | 4.53 | 60.54 |
| Hyp13-β | 2.17/1.68 | 37.32 |
| Hyp13-γ | 4.21 | 69.00 |
| Hyp13-γOH | broad | — |
| Hyp13-δ | 3.69/3.38 | 56.45 |
| Hyp13-C' | — | 172.83 |
| Aib14-NH | 7.94 | — |
| Aib14-α | — | 55.64 |
| Aib14-β | 1.39 | 23.51 |
| Aib14-β' | 1.33 | 25.66 |
| Aib14-C' | — | 171.71 |
| Pro15-α | 4.13 | 61.78 |
| Pro15-β | 1.85/1.17 | 28.33 |
| Pro15-γ | 1.59/1.48 | 24.82 |
| Pro15-δ | 3.80/3.51 | 47.36 |
| Pro15-C' | — | 170.68 |
| Phe16-NH | 7.15 | — |
| Phe16-α | 3.84 | 52.58 |
| Phe16-β | 2.98/2.58 | 36.35 |
| Phe16-γ | — | 139.47 |
| Phe16-δ | 7.26 | 129.33 |
| Phe16-ε | 7.26 | 127.92 |
| Phe16-ξ | 7.14 | 125.64 |
| Phe16-CH$_2$—OH | 3.39/3.25 | 63.38 |
| Phe16-CH$_2$—OH | broad | — |

TABLE 6

NMR data (chemical shifts) for cephaibol P in DMSO at 300° K.

| Proton | $^1$H |
|---|---|
| Ac-Me | 1.83 |
| Ac-C' | — |
| Phe1-NH | 8.23 |
| Phe1-α | 4.48 |
| Phe1-β | 3.05/2.84 |
| Phe1-δ | 7.27 |
| Phe1-ε | 7.27 |
| Phe1-ξ | 7.19 |
| Iva2-NH | 8.28 |
| Iva2-β | 1.86/1.66 |
| Iva2-γ | 0.74 |
| Iva2-αMe | 1.27 |
| Gln3-NH | 8.14 |
| Gln3-α | 3.97 |
| Gln3-β | 1.88 |
| Gln3-γ | 2.18 |
| Gln3-ε-NH$_2$ | 7.34/6.88 |
| Aib4-NH | 7.99 |
| Aib4-β | 1.39 |

TABLE 6-continued

NMR data (chemical shifts) for cephaibol P in DMSO at 300° K.

| Proton | $^1$H |
|---|---|
| Aib4-β' | 1.35 |
| Ile5-NH | 7.53 |
| Ile5-α | 3.88 |
| Ile5-β | 1.88 |
| Ile5-γMe | 0.84 |
| Ile5-γ | 1.45/1.18 |
| Ile5-δ | 0.78 |
| Thr6-NH | 7.60 |
| Thr6-α | 3.82 |
| Thr6-β | 4.09 |
| Thr6-γ | 1.12 |
| Thr6-OH | 4.96 |
| Aib7-NH | 7.77 |
| Aib7-β | 1.36 |
| Aib7-β' | 1.36 |
| Leu8-NH | 7.26 |
| Leu8-α | 4.21 |
| Leu8-β | 1.65/1.56 |
| Leu8-γ | 1.68 |
| Leu8-δ | 0.85 |
| Leu8-δ' | 0.78 |
| Aib9-NH | 7.94 |
| Aib9-β | 1.52 |
| Aib9-β' | 1.42 |
| Hyp10-α | 4.39 |
| Hyp10-β | 2.16/1.77 |
| Hyp10-γ | 4.26 |
| Hyp10-γOH | 5.12 |
| Hyp10-δ | 3.76/3.44 |
| Gln11-NH | 7.85 |
| Gln11-α | 4.22 |
| Gln11-β | 1.89 |
| Gln11-γ | 2.14/2.12 |
| Gln11-ε-NH$_2$ | 7.20/6.70 |
| Aib12-NH | 7.79 |
| Aib12-β | 1.51 |
| Aib12-β' | 1.39 |
| Hyp13-α | 4.53 |
| Hyp13-β | 2.18/1.71 |
| Hyp13-γ | 4.22 |
| Hyp13-γOH | 5.09 |
| Hyp13-δ | 3.67/3.38 |
| Aib14-NH | 8.07 |
| Aib14-β | 1.47 |
| Aib14-β' | 1.38 |
| Pro15-α | 4.17 |
| Pro15-β | 1.90/1.04 |
| Pro15-γ | 1.63/1.51 |
| Pro15-δ | 3.87/3.58 |
| Pro15-C' | — |
| Phe16-NH | 7.67 |
| Phe16-α | 4.35 |
| Phe16-β | 3.26/2.80 |
| Phe16-δ | 7.32 |
| Phe16-ε | 7.26 |
| Phe16-ξ | 7.19 |
| Ser17-NH | 7.39 |
| Ser17-α | 4.24 |
| Ser17-β | 3.71 |
| Ser17-βOH | 4.77(broad) |

TABLE 7

NMR data (chemical shifts) for cephaibol Q in DMSO at 300° K.

| Proton | $^1$H |
|---|---|
| Ac-Me | 1.83 |
| Ac—C' | — |
| Phe1-NH | 8.23 |
| Phe1-α | 4.48 |
| Phe1-β | 3.05/2.84 |
| Phe1-δ | 7.27 |

TABLE 7-continued

NMR data (chemical shifts) for cephaibol Q in DMSO at 300° K.

| Proton | $^1$H |
|---|---|
| Phe1-ε | 7.27 |
| Phe1-ξ | 7.19 |
| Iva2-NH | 8.28 |
| Iva2-β | 1.86/1.66 |
| Iva2-γ | 0.74 |
| Iva2-αMe | 1.27 |
| Gln3-NH | 8.14 |
| Gln3-α | 3.97 |
| Gln3-β | 1.88 |
| Gln3-γ | 2.18 |
| Gln3-ε-NH$_2$ | 7.34/6.88 |
| Aib4-NH | 7.99 |
| Aib4-β | 1.39 |
| Aib4-β' | 1.35 |
| Ile5-NH | 7.53 |
| Ile5-α | 3.88 |
| Ile5-β | 1.88 |
| Ile5-γMe | 0.84 |
| Ile5-γ | 1.45/1.18 |
| Ile5-δ | 0.78 |
| Thr6-NH | 7.60 |
| Thr6-α | 3.83 |
| Thr6-β | 4.09 |
| Thr6-γ | 1.11 |
| Thr6-OH | 4.96 |
| Aib7-NH | 7.74 |
| Aib7-β | 1.36 |
| Aib7-β' | 1.36 |
| Leu8-NH | 7.28 |
| Leu8-α | 4.16 |
| Leu8-β | 1.65/1.56 |
| Leu8-γ | 1.69 |
| Leu8-δ | 0.85 |
| Leu8-δ' | 0.78 |
| Aib9-NH | 7.97 |
| Aib9-β | 1.50 |
| Aib9-β' | 1.42 |
| Pro10-α | 4.30 |
| Pro10-β | 2.22/1.69 |
| Pro10-γ | 1.84 |
| Pro10-δ | 3.75/3.53 |
| Gln11-NH | 7.79 |
| Gln11-α | 4.24 |
| Gln11-β | 1.88 |
| Gln11-γ | 2.14/2.12 |
| Gln11-ε-NH$_2$ | 7.19/6.71 |
| Aib12-NH | 7.78 |
| Aib12-β | 1.50 |
| Aib12-β' | 1.39 |
| Hyp13-α | 4.53 |
| Hyp13-β | 2.18/1.71 |
| Hyp13-γ | 4.22 |
| Hyp13-γOH | 5.09 |
| Hyp13-δ | 3.67/3.38 |
| Aib14-NH | 8.07 |
| Aib14-β | 1.47 |
| Aib14-β' | 1.38 |
| Pro15-α | 4.17 |
| Pro15-β | 1.90/1.04 |
| Pro15-γ | 1.63/1.51 |
| Pro15-δ | 3.87/3.58 |
| Pro15-C' | — |
| Phe16-NH | 7.67 |
| Phe16-α | 4.35 |
| Phe16-β | 3.26/2.80 |
| Phe16-δ | 7.32 |
| Phe16-ε | 7.26 |
| Phe16-ξ | 7.19 |
| Ser17-NH | 7.39 |
| Ser17-α | 4.24 |
| Ser17-β | 3.71 |
| Ser17-βOH | 4.77 (broad) |

Example 10

Determination of Anthelmintic Action

For the testing of the action of the cephaibols on helminths, an in vitro test (larval development test) was carried out with larvae of the chicken roundworm *Ascaridia galli*. Embryonate eggs of *A. galli* were surface-sterilized by treatment with 5% strength sodium hypochlorite solution and, after removal of this solution, mechanically opened by means of rotating glass beads (5 mm). The hatched L2 larvae were enriched via larval enrichment processes, taken up in nutrient medium and incubated at 41° C. and 10% $CO_2$.

48 hours after hatching, the larvae were incubated (41° C., 10% $CO_2$) in microtiter plates (96 well) for 5 days with medicated medium (200 µl) in the concentrations 200, 100, 50 . . . 0.1 µg/ml. During the 5-day incubation period, motility, morphology, and vitality were checked microscopically and documented on a daily basis. After medication, the larval culture was incubated for 48 hours with Neutral Red in a concentration of 0.16%; after removal of the Neutral Red by change of medium, the enrichment of the vital dye in the intestine of the larvae was assessed as an index for active food intake and thus as proof of the vitality. The medication of the larvae with cephaibol A in the concentrations 200, 100, 50, and 25 µg/ml led to 100% mortality; at a concentration of 12.5 µg/ml and 6.25 µg/ml, the mortality was 92% and 20% respectively.

Example 11

Action on Ectoparasites

The action against ectoparasites was checked in the flea larval test (cat flea=*Ctenocephalides felis*). 5 mg of cephaibol A were dissolved in 0.5 ml of acetone and mixed into 500 mg of blood meal (defibrinated sheep blood). After the solvent had evaporated, 2 g of quartz sand were mixed with medicated blood meal such that preparation concentrations of 2000, 1000, 500, 250 ppm etc. resulted. 15 flea eggs per medicated sample or solvent control were added to the mixture of medicated blood meal and quartz sand, which was then incubated at 37° C. and high atmospheric humidity. The larval development, pupation and development to the adult stage were checked at an interval of 3–5 days and the mortality rates were documented.

Depending on the dose, a larvicidal action of >90% in comparison with the solvent control was observed.

Example 12

Determination of the Antimicrobial Action

Table 8 shows some minimal inhibitory concentrations (MIC) of the antimicrobial spectrum.

TABLE 8

The minimal inhibitory concentrations (MIC) of cephaibol A against some selected microorganisms.

| Strain | MIC [µg/ml] |
|---|---|
| *Enterococcus hirae* ATCC 10541 | 64 |
| *Enterococcus faecalis* ATCC 29212 | 64 |
| *Enterobacter cloacae* P 99 | >128 |
| *Enterobacter cloacae* 1321 E | >128 |
| *Escherichia coli* TEM | >128 |
| *Escherichia coli* 1507 E | >128 |
| *Escherichia coli* DC 0 | >128 |
| *Escherichia coli* DC 2 | >128 |
| *Escherichia coli* ATCC 25922 | >128 |
| *Klebsiella aerogenes* 1082 E | >128 |
| *Klebsiella oxytoca* 1522 E | >128 |
| *Pseudomonas aeruginosa* 77/2 | >128 |
| *Pseudomonas aeruginosa* 1771 | >128 |
| *Pseudomonas aeruginosa* 1771 M | >128 |
| *Pseudomonas aeruginosa* ATCC 9027 | >128 |
| *Pseudomonas aeruginosa* ATCC 27853 | >128 |
| *Staphylococcus aureus* 285 | 8 |
| *Staphylococcus aureus* ATCC 29213 | 16 |
| *Streptococcus pyogenes* 308 A | 32 |
| *Streptococcus pyogenes* 77 A | >128 |
| *Bordetella bronchiseptica* ATCC 4617 | >128 |
| *Pasteurella multocida* 3;tox.pos. | >128 |
| *Pasteurella haemolytica* 7 | >128 |
| *Bordetella bronchiseptica* 9 | >128 |
| *Bordetella bronchiseptica* 10 | >128 |
| *Pasteurella multocida* P 48 | >128 |
| *Pasteurella haemolytica* P 53 | >128 |
| *Mycoplasma gallisepticum* | 64 |
| *Mycoplasma mycoides* LC | 128 |
| *Mycoplasma mycoides* L | 64 |

The invention claimed is:

1. A method for treatment of infections comprising administering to a host in need thereof an amount of one or more compounds of the formula I (SEQ ID NO:9)

AcPhe-Aib-Aib-Aib-x-w-Leu-y-Aib-Hyp-Gln-z-Hyp-Aib-Pro-R     (I)

wherein R is Phe-ol or Phe-al and w, x, y, and z have the following meanings:
- a) w is Gly or Ala; x is Aib; and y and z are Iva;
- b) w is Gly; x, y and z are Iva;
- c) w is Gly; x and z are Aib; and y is Iva;
- d) w is Gly; x, y and z are Aib; or
- e) w is Gly; x and y are Aib; and z is Iva;

or a compound of the formula II (SEQ ID NO: 10)

AcPhe-Iva-Gln-Aib-Ile-Thr-Aib-Leu-Aib-x-Gln-Aib-Hyp-Aib-Pro-Phe-Ser     (II)

wherein x is Hyp or Pro;
or a physiologically tolerable salt thereof effective to treat or a bacterial, helminth, fungal, and/or protozoal infection.

2. A method for treatment of infections comprising administering to a host in need thereof an amount of a pharmaceutical composition effective to treat a bacterial, helminth, fungal or protozoal infection; wherein the pharmaceutical composition comprises at least one compound of claim 1, and at least one suitable carrier or an excipient.

3. The method of claim 1 wherein the host suffers from or is at risk of developing a bacterial infection.

4. The method of claim 3, wherein the bacterial infection results from a human or animal parasite.

5. The method of claim 1 wherein the host suffers from or is at risk of developing a human-pathogenic or animal-pathogenic endoparasite and/or ectoparasite infection.

6. The method of claim 5, wherein the human-pathogenic or animal-pathogenic endoparasite and/or ectoparasite belongs to the class of arachnids.

7. The method of claim 5, wherein the human-pathogenic or animal-pathogenic endoparasite and/or ectoparasite belongs to the class of insects.

8. The method of claim 1 wherein the host suffers from or is at risk of developing a helminth infection.

9. The method of claim 8, wherein the helminth is a trematode, cestode, or nematode.

10. The method of claim 1 wherein the host suffers from or is at risk of developing a fungal infection.

11. The method of claim 1, wherein the host suffers from or is at risk of developing a protozoal infection.

12. The method of claim 11, wherein the host is infected by or is at risk of developing an infection from plasmodia, trypanosomes, amoebae, trichomonads, and/or toxoplasmae.

* * * * *

UNITED STATES PATENT AND TRADEMARK OFFICE
CERTIFICATE OF CORRECTION

PATENT NO. : 7,067,112 B2
APPLICATION NO. : 10/411144
DATED : June 27, 2006
INVENTOR(S) : Laszlo Vertesy et al.

It is certified that error appears in the above-identified patent and that said Letters Patent is hereby corrected as shown below:

In claim 1, col. 47, lines 46-47, "effective to treat or a" should read --effective to treat a--.

In claim 2, col. 47, line 54, "carrier or an excipient" should read --carrier or excipient--.

Signed and Sealed this

Sixth Day of March, 2007

JON W. DUDAS
*Director of the United States Patent and Trademark Office*

```
                         SEQUENCE LISTING

<160> NUMBER OF SEQ ID NOS: 10

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
<222> LOCATION: (8)
<223> OTHER INFORMATION: Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Iva
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 1

Xaa Xaa Xaa Xaa Xaa Gly Leu Xaa Xaa Xaa Gln Xaa Xaa Xaa Pro Xaa
 1               5                  10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(4)
<223> OTHER INFORMATION: Aib
<220> FEATURE:
<221> NAME/KEY: MOD_RES
<222> LOCATION: (5)
<223> OTHER INFORMATION: Iva
<220> FEATURE:
<221> NAME/KEY: MOD_RES
<222> LOCATION: (8)
<223> OTHER INFORMATION: Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Iva
<220> FEATURE:
<221> NAME/KEY: MOD_RES
<222> LOCATION: (13)
```

-continued

```
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 2

Xaa Xaa Xaa Xaa Xaa Gly Leu Xaa Xaa Xaa Gln Xaa Xaa Xaa Pro Xaa
 1               5                  10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
<222> LOCATION: (8)
<223> OTHER INFORMATION: Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 3

Xaa Xaa Xaa Xaa Xaa Gly Leu Xaa Xaa Xaa Gln Xaa Xaa Xaa Pro Xaa
 1               5                  10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
```

```
<222> LOCATION: (2)..(5)
<223> OTHER INFORMATION: Aib
<220> FEATURE:
<221> NAME/KEY: MOD_RES
<222> LOCATION: (8)..(9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 4

Xaa Xaa Xaa Xaa Xaa Gly Leu Xaa Xaa Xaa Gln Xaa Xaa Xaa Pro Xaa
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
<222> LOCATION: (8)..(9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Iva
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 5

Xaa Xaa Xaa Xaa Xaa Gly Leu Xaa Xaa Xaa Gln Xaa Xaa Xaa Pro Xaa
 1               5                  10                  15
```

```
<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)
<223> OTHER INFORMATION: Iva
<220> FEATURE:
<221> NAME/KEY: MOD_RES
<222> LOCATION: (4)
<223> OTHER INFORMATION: Aib
<220> FEATURE:
<221> NAME/KEY: MOD_RES
<222> LOCATION: (7)
<223> OTHER INFORMATION: Aib
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib

<400> SEQUENCE: 6

Xaa Xaa Gln Xaa Ile Thr Xaa Leu Xaa Xaa Gln Xaa Xaa Xaa Pro Phe
 1               5                  10                  15

Ser

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)
<223> OTHER INFORMATION: Iva
<220> FEATURE:
<221> NAME/KEY: MOD_RES
<222> LOCATION: (4)
<223> OTHER INFORMATION: Aib
<220> FEATURE:
<221> NAME/KEY: MOD_RES
<222> LOCATION: (7)
<223> OTHER INFORMATION: Aib
<220> FEATURE:
<221> NAME/KEY: MOD_RES
<222> LOCATION: (9)
<223> OTHER INFORMATION: Aib
```

```
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib

<400> SEQUENCE: 7

Xaa Xaa Gln Xaa Ile Thr Xaa Leu Xaa Pro Gln Xaa Xaa Xaa Pro Phe
 1               5                  10                  15

Ser

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(5)
<223> OTHER INFORMATION: Aib
<220> FEATURE:
<221> NAME/KEY: MOD_RES
<222> LOCATION: (8)
<223> OTHER INFORMATION: Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Iva
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol

<400> SEQUENCE: 8

Xaa Xaa Xaa Xaa Xaa Ala Leu Xaa Xaa Xaa Gln Xaa Xaa Xaa Pro Xaa
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)..(4)
<223> OTHER INFORMATION: Aib
<220> FEATURE:
<221> NAME/KEY: MOD_RES
<222> LOCATION: (5)
<223> OTHER INFORMATION: Aib or Iva
<220> FEATURE:
<221> NAME/KEY: MOD_RES
<222> LOCATION: (6)
<223> OTHER INFORMATION: Gly or Ala
<220> FEATURE:
<221> NAME/KEY: MOD_RES
<222> LOCATION: (8)
<223> OTHER INFORMATION: Aib or Iva
<220> FEATURE:
<221> NAME/KEY: MOD_RES
<222> LOCATION: (9)
<223> OTHER INFORMATION: Aib
<220> FEATURE:
<221> NAME/KEY: MOD_RES
<222> LOCATION: (10)
<223> OTHER INFORMATION: Hyp
<220> FEATURE:
<221> NAME/KEY: MOD_RES
<222> LOCATION: (12)
<223> OTHER INFORMATION: Aib or Iva
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<221> NAME/KEY: MOD_RES
<222> LOCATION: (16)
<223> OTHER INFORMATION: Phe-ol or Phe-al
<220> FEATURE:
<223> OTHER INFORMATION: see specification as filed for detailed
      description of substitutions and preferred embodiments

<400> SEQUENCE: 9

Xaa Xaa Xaa Xaa Xaa Xaa Leu Xaa Xaa Xaa Gln Xaa Xaa Xaa Pro Xaa
 1               5                  10                  15

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: AcPhe
<220> FEATURE:
<221> NAME/KEY: MOD_RES
<222> LOCATION: (2)
<223> OTHER INFORMATION: Iva
<220> FEATURE:
<221> NAME/KEY: MOD_RES
<222> LOCATION: (4)
<223> OTHER INFORMATION: Aib
<220> FEATURE:
<221> NAME/KEY: MOD_RES
<222> LOCATION: (7)
<223> OTHER INFORMATION: Aib
<220> FEATURE:
<221> NAME/KEY: MOD_RES
<222> LOCATION: (9)
```

```
<223> OTHER INFORMATION: Aib
<220> FEATURE:
<221> NAME/KEY: MOD_RES
<222> LOCATION: (10)
<223> OTHER INFORMATION: Hyp or Pro
<220> FEATURE:
<221> NAME/KEY: MOD_RES
<222> LOCATION: (12)
<223> OTHER INFORMATION: Aib
<220> FEATURE:
<221> NAME/KEY: MOD_RES
<222> LOCATION: (13)
<223> OTHER INFORMATION: Hyp
<220> FEATURE:
<221> NAME/KEY: MOD_RES
<222> LOCATION: (14)
<223> OTHER INFORMATION: Aib
<220> FEATURE:
<223> OTHER INFORMATION: see specification as filed for detailed
      description of substitutions and preferred embodiments

<400> SEQUENCE: 10

Xaa Xaa Gln Xaa Ile Thr Xaa Leu Xaa Xaa Gln Xaa Xaa Xaa Pro Phe
 1               5                  10                  15

Ser
```